United States Patent [19]  [11] 4,322,435
Kojima et al.  [45] Mar. 30, 1982

[54] PROSTACYCLIN COMPOUNDS
[75] Inventors: Koichi Kojima; Kiyoshi Sakai; Shinsaku Kobayashi, all of Hiromachi, Japan
[73] Assignee: Sankyo Company Limited, Tokyo, Japan
[21] Appl. No.: 153,825
[22] Filed: May 27, 1980

Related U.S. Application Data
[62] Division of Ser. No. 1,418, Jan. 8, 1979.

[30] Foreign Application Priority Data
Jan. 6, 1978 [JP] Japan .................................. 53-462

[51] Int. Cl.$^3$ ............................................ C07C 177/00
[52] U.S. Cl. .................................. 424/305; 542/426; 424/317; 560/119; 562/501; 568/374
[58] Field of Search ................. 560/119; 562/501; 424/305, 317

[56] References Cited
U.S. PATENT DOCUMENTS
4,064,351  12/1977  Sakai et al. .......................... 560/121

FOREIGN PATENT DOCUMENTS
2017699  10/1979  United Kingdom .

Primary Examiner—Robert Gerstl
Attorney, Agent, or Firm—Frishauf, Holtz, Goodman & Woodward

[57] ABSTRACT

Prostacyclin derivatives of formula (I):

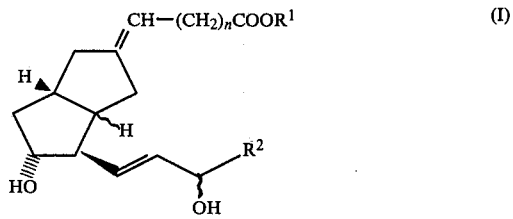

(wherein $R^1$ represents a hydrogen atom or a lower alkyl group; $R^2$ represents an alkenyl group having from 8 to 12 carbon atoms; and n represents an integer of from 1 to 8, inclusive) and pharmaceutically acceptable salts thereof, are valuable pharmaceuticals, showing excellent thrombocyte agglutination inhibitory, coronary blood vessel dilatory and bronchodilatory effects, and may be prepared by introducing the =CH(CH$_2$)$_n$COOR$^1$ side chain onto an appropriate compound by means of a Wittig reaction.

22 Claims, No Drawings

PROSTACYCLIN COMPOUNDS

This is a division of application Ser. No. 1,418 filed Jan. 8, 1979.

BACKGROUND OF THE INVENTION

The prostaglandins are a well known group of compounds which have been shown to have a variety of valuable pharmacological activities. Recently, prostacyclin (PGI$_2$) has been discovered and shown to have strong platelet aggregation inhibitory activity; unfortunately, prostacyclin is rather unstable and is rapidly hydrolized to the stable, but less active, 6-oxoprostaglandin F$_{1\alpha}$. We have now discovered a series of prostacyclin derivatives, whose activities are comparable with those of prostacyclin and prostaglandin E$_1$ (PGE$_1$), but which are much more stable than prostacyclin and PGE$_1$.

BRIEF SUMMARY OF INVENTION

Thus, the present invention consists in prostacyclin derivatives of formula (I):

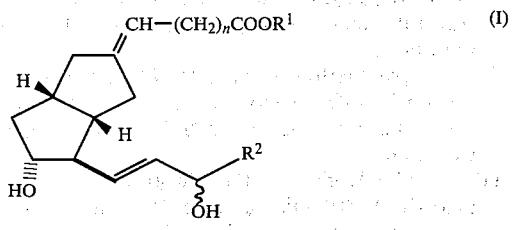

(wherein: R$^1$ represents a hydrogen atom or a lower alkyl group; R$^2$ represents an alkyl group or an alkenyl group; and n represents an integer of from 1 to 8, inclusive and pharmacologically acceptable salts thereof.

The invention also provides pharmaceutical compositions comprising the prostacyclin derivatives of formula (I) in admixture with a pharmaceutically acceptable carrier or diluent.

The invention still further provides a process for preparing the prostacyclin derivatives of formula (I) which comprises reacting a compound of formula (II):

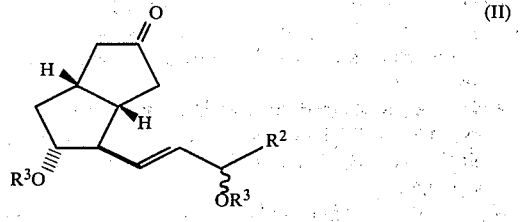

(wherein R$^2$ is as defined above and R$^3$ represents a hydroxy-protecting group) with a Wittig reagent of general formula (III):

$(R^4)_3P^\oplus$—$C^\ominus H$—$(CH_2)_n COOM$   (III)

(wherein: R$^4$ represents an aryl group or an alkyl group; M represents an alkali metal atom; and n is as defined above), converting the product thus obtained into a free acid by treatment with an acid, optionally esterifying the free acid to produce a compound of formula (IV):

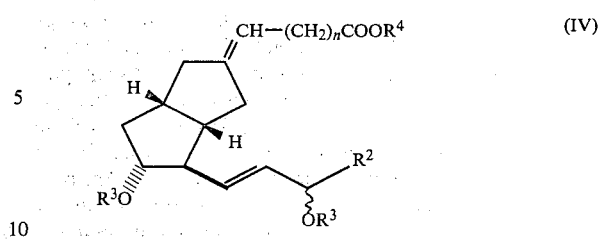

(wherein R$^1$, R$^2$, R$^3$ and n are as defined above), removing the hydroxy-protecting groups and, if necessary, hydrolizing the ester. Where the product is an acid, this may, if desired, be salified by conventional techniques.

DETAILED DESCRIPTION OF INVENTION

In the compounds described above, R$^1$ represents a hydrogen atom or a lower alkyl group. The term "lower alkyl" is here defined to mean an alkyl group containing from 1 to 15 carbon atoms. The lower alkyl group may be straight or branched chain and preferably contains from 1 to 5 carbon atoms. Examples of such groups include the hexyl, heptyl, n-octyl, 2-methyloctyl, n-nonyl, 2-methylnonyl, 2-ethyloctyl, n-decyl, 2-ethyldecyl, dodecyl, 2-pentylheptyl tridecyl, tetradecyl, 2-hexyloctyl and pentadecyl groups, preferably the methyl, ethyl, n-propyl, ispropyl, n-butyl, isobutyl, n-pentyl and isopentyl groups.

R$^2$ represents an alkyl or alkenyl group and these may be straight-chain or branched chain groups. The alkyl group preferably contains from 1 to 12 carbon atoms and examples include the methyl, ethyl, n-propyl, isopropyl, n-butyl, isobutyl, n-pentyl, isopentyl, 1-methylpentyl, 2-methylpentyl, n-hexyl, n-heptyl, 1,1-dimethylpentyl, 2-ethylpentyl, n-octyl, 2-methyloctyl, n-nonyl, 2-methylnonyl, 2-ethyloctyl, n-decyl, 2-methyldecyl, and 2-ethyldecyl groups. The alkenyl group preferably contains from 2 to 12 carbon atoms and examples include the vinyl, allyl, 2-butenyl, 3-pentenyl, 2-methyl-3-pentenyl, 4-hexenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl and 2,6-diethyl-5-octenyl groups.

Particularly preferred compounds of formula (I) are those in which: R$^1$ represents a hydrogen atom or an alkyl group having from 1 to 3 carbon atoms (methyl, ethyl, n-propyl or isopropyl); R$^2$ represents an alkyl group having from 4 to 10 carbon atoms (e.g. butyl, isobutyl, n-pentyl, isopentyl, 1-methylpentyl, 2-methylpentyl, n-hexyl, n-heptyl, 1,1-dimethylpentyl, 2-ethylpentyl, n-octyl, 2-methyloctyl or 2-ethyloctyl) or an alkenyl group having from 5 to 12 carbon atoms (e.g. 3-pentyl, 2-methyl-3-pentyl, 4-hexenyl, 5-heptenyl, 6-methyl-5-heptenyl, 2,6-dimethyl-5-heptenyl, 1,1,6-trimethyl-5-heptenyl, 6-methyl-5-octenyl, 2,6-dimethyl-5-octenyl, 6-ethyl-5-octenyl, 2-methyl-6-ethyl-5-octenyl or 2,6-diethyl-5-octenyl); and n represents an integer of from 1 to 5, inclusive.

The compounds of formula (I) in which R$^1$ represents a hydrogen atom may be converted to a pharmacologically acceptable salt, if required. Examples of such salts include: salts of alkali metals, e.g. sodium or potassium; salts of alkaline earth metals, e.g. magnesium or calcium; ammonium salts; quarternary ammonium salts, such as tetramethylammonium salts, tetraethylammonium salts, benzyltrimethylammonium salts or phenyltriethylammonium salts; salts of lower aliphatic amines, lower alicyclic amines or lower aralkylamines, such as methylamine, ethylamine, dimethylamine, diethylamine, trimethylamine, triethylamine, N-methylhexylamine, cyclopentylamine, dicyclohexylamine, benzylamine, dibenzylamine, α-phenylethylamine, or ethylene diamine; salts of heterocyclic amines and their lower alkyl derivatives, such as piperidine, morpholine, pyrrolidine, piperazine, pyridine, 1-methylpiperazine, or 4-ethylmorpholine; and salts of amines containing a hydrophilic group, such as monoethanolamine, ethyldiethanolamine or 2-amino-1-butanol.

The compounds of formula (I) can exist in the form of various stereoisomers, depending upon: the conformation of the hydroxy group in the side chain attached to the cyclopentane ring (the 15-hydroxy group, using the numbering system for prostaglandins); the double bond attached to the other cyclopentane ring (at the 5-position, in the prostaglandin numbering system); and, where $R^2$ represents an alkenyl group, the double bond in $R^2$. Where a compound of formula (I) is obtained as a mixture of these stereoisomers, individual isomers can be obtained by conventional separation and resolution techniques. Although all of these stereoisomers are represented by a single formula (I), the present invention covers both the individual isomers and mixtures thereof.

Examples of preferred compounds in accordance with the present invention are listed below:

(1) 6,9α-Methylene-11α,15α-dihydroxyprost-5(Z),13(E)-dienoic acid; its sodium and potassium salts; and its methyl, ethyl, n-propyl and isopropyl esters.

(2) 6,9α-Methylene-11α,15β-dihydroxyprost-5(Z),13(E)-dienoic acid; its sodium and potassium salts; and its methyl, ethyl, n-propyl and isopropyl esters.

(3) 6,9α-Methylene-11α,15α-dihydroxyprost-5(E),13(E)-dienoic acid; its sodium and potassium salts; and its methyl, ethyl, n-propyl and isopropyl esters.

(4) 6,9α-Methylene-11α,15β-dihydroxyprost-5(E),13(E)-dienoic acid; its sodium and potassium salts; and its methyl, ethyl, n-propyl and isopropyl esters.

(5) 6,9α-Methylene-11α,15α-dihydroxy-4-norprost-5(Z),13(E)-dienoic acid; its sodium and potassium salts; and its methyl, ethyl, n-propyl and isopropyl esters.

(6) 6,9α-Methylene-11α-15β-dihydroxy-4-norprost-5(Z),13(E)-dienoic acid; its sodium and potassium salts; and its methyl, ethyl, n-propyl and isopropyl esters.

(7) 6,9α-Methylene-11α,15α-dihydroxy-4-norprost-5(E),13(E)-dienoic acid; its sodium and potassium salts; and its methyl, ethyl, n-propyl and isopropyl esters.

(8) 6,9α-Methylene-11α-15β-dihydroxy-4-norprost-5(E),13(E)-dienoic acid; its sodium and potassium salts; and its methyl, ethyl, n-propyl and isopropyl esters.

(9) 6,9α-Methylene-11α,15α-dihydroxy-3,4-dinorprost-5(Z),13(E)-dienoic acid; its sodium and potassium salts; and its methyl, ethyl, n-propyl and isopropyl esters.

(10) 6,9α-Methylene-11α,15β-dihydroxy-3,4-dinorprost-5(Z),13(E)-dienoic acid; its sodium and potassium salts; and its methyl, ethyl, n-propyl and isopropyl esters.

(11) 6,9α-Methylene-11α,15α-dihydroxy-3,4-dinorprost-5(E),13(E)-dienoic acid; its sodium and potassium salts; and its methyl, ethyl, n-propyl and isopropyl esters.

(12) 6,9α-Methylene-11α,15β-dihydroxy-3,4-dinorprost-5(E),13(E)-dienoic acid; its sodium and potassium salts; and its methyl, ethyl, n-propyl and isopropyl esters.

(13) 6,9α-Methylene-11α,15α-dihydroxy-20-norprost-5(Z),13(E)-dienoic acid; its sodium and potassium salts; and its methyl, ethyl, n-propyl and isopropyl esters.

(14) 6,9α-Methylene-11α,15β-dihydroxy-20-norprost-5(Z),13(E)-dienoic acid; its sodium and potassium salts; and its methyl, ethyl, n-propyl and isopropyl esters.

(15) 6,9α-Methylene-11α,15α-dihydroxy-20-norprost-5(E),13(E)-dienoic acid; its sodium and potassium salts; and its methyl, ethyl, n-propyl and isopropyl esters.

(16) 6,9α-Methylene-11α,15β-dihydroxy-20-norprost-5(E),13(E)-dienoic acid; its sodium and potassium salts; and its methyl, ethyl, n-propyl and isopropyl esters.

(17) 6,9α-Methylene-11α,15α-dihydroxy-20-methylprost-5(Z),13(E)-dienoic acid; its sodium and potassium salts; and its methyl, ethyl, n-propyl and isopropyl esters.

(18) 6,9α-Methylene-11α,15β-dihydroxy-20-methylprost-5(Z),13(E)-dienoic acid; its sodium and potassium salts; and its methyl, ethyl, n-propyl and isopropyl esters.

(19) 6,9α-Methylene-11α,15α-dihydroxy-20-methylprost-5(E),13(E)-dienoic acid; its sodium and potassium salts; and its methyl, ethyl, n-propyl and isopropyl esters.

(20) 6,9α-Methylene-11α-15β-dihydroxy-20-methylprost-5(E),13(E)-dienoic acid; its sodium and potassium salts; and its methyl, ethyl, n-propyl and isopropyl esters.

(21) 6,9α-Methylene-11α,15α-dihydroxy-17-methylprost-5(Z), 13(E)-dienoic acid; its sodium and potassium salts; and its methyl, ethyl, n-propyl and isopropyl esters.

(22) 6,9α-Methylene-11α,15β-dihydroxy-17-methylprost-5(Z), 13(E)-dienoic acid; its sodium and potassium salts; and its methyl, ethyl, n-propyl and isopropyl esters.

(23) 6,9α-Methylene-11α,15α-dihydroxy-17-methylprost-5(E), 13(E)-dienoic acid; its sodium and potassium salts; and its methyl, ethyl, n-propyl and isopropyl esters.

(24) 6,9α-Methylene-11α,15β-dihydroxy-17-methylprost-5(E), 13(E)-dienoic acid; its sodium and potassium salts; and its methyl, ethyl, n-propyl and isopropyl esters.

(25) 6,9α-Methylene-11α,15α-dihydroxy-16,16-dimethylprost-5(Z)-13(E)-dienoic acid; its sodium and potassium salts; and its methyl, ethyl, n-propyl and isopropyl esters.

(26) 6,9α-Methylene-11α,15β-dihydroxy-16,16-dimethylprost-5(Z)-13(E)-dienoic acid; its sodium and potassium salts; and its methyl, ethyl, n-propyl and isopropyl esters.

(27) 6,9α-Methylene-11α,15α-dihydroxy-16,16-dimethylprost-5(E)-13(E)-dienoic acid; its sodium and potassium salts; and its methyl, ethyl, n-propyl and isopropyl esters.

(28) 6,9α-Methylene-11α,15β-dihydroxy-16,16-dimethylprost-5(E)-13(E)-dienoic acid; its sodium and potassium salts; and its methyl, ethyl, n-propyl and isopropyl esters.
(29) 6,9α-Methylene-11α,15α-dihydroxy-20-ethylprost-5(Z),13(E)-dienoic acid; its sodium and potassium salts; and its methyl, ethyl, n-propyl and isopropyl esters.
(30) 6,9α-Methylene-11α,15β-dihydroxy-20-ethylprost-5(Z),13(E)-dienoic acid; its sodium and potassium salts; and its methyl, ethyl, n-propyl and isopropyl esters.
(31) 6,9α-Methylene-11α,15α-dihydroxy-20-ethylprost-5(E),13(E)-dienoic acid; its sodium and potassium salts; and its methyl, ethyl, n-propyl and isopropyl esters.
(32) 6,9α-Methylene-11α,15β-dihydroxy-20-ethylprost-5(E),13(E)-dienoic acid; its sodium and potassium salts; and its methyl, ethyl, n-propyl and isopropyl esters.
(33) 6,9α-Methylene-11α,15α-dihydroxy-20-methylprost-5(Z),13(E),19-trienoic acid; its sodium and potassium salts; and its methyl, ethyl, n-propyl and isopropyl esters.
(34) 6,9α-Methylene-11α,15β-dihydroxy-20-methylprost-5(Z),13(E), 19-trienoic acid; its sodium and potassium salts; and its methyl, ethyl, n-propyl and isopropyl esters.
(35) 6,9α-Methylene-11α,15α-dihydroxy-20-methylprost-5(E),13(E),19-trienoic acid; its sodium and potassium salts; and its methyl, ethyl, n-propyl and isopropyl esters.
(36) 6,9α-Methylene-11α,15β-dihydroxy-20-methylprost-5(E),13(E),19-trienoic acid; its sodium and potassium salts; and its methyl, ethyl, n-propyl and isopropyl esters.
(37) 6,9α-Methylene-11α,15α-dihydroxy-20-isopropylideneprost-5(Z),13(E)-dienoic acid; its sodium and potassium salts; and its methyl, ethyl, n-propyl and isopropyl esters.
(38) 6,9α-Methylene-11α,15β-dihydroxy-20-isopropylideneprost-5(Z),13(E)-dienoic acid; its sodium and potassium salts; and its methyl, ethyl, n-propyl and isopropyl esters.
(39) 6,9α-Methylene-11α,15α-dihydroxy-20-isopropylideneprost-5(E),13(E)-dienoic acid; its sodium and potassium salts; and its methyl, ethyl, n-propyl and isopropyl esters.
(40) 6,9α-Methylene-11α,15β-dihydroxy-20-isopropylideneprost-5(E),13(E)-dienoic acid; its sodium and potassium salts; and its methyl, ethyl, n-propyl and isopropyl esters.
(41) 6,9α-Methylene-11α,15α-dihydroxy-17methyl-20-isopropylideneprost-5(Z),13(E)-dienoic acid; its sodium and potassium salts; and its methyl, ethyl, n-propyl and isopropyl esters.
(42) 6,9α-Methylene-11α,15β-dihydroxy-17-methyl-20-isopropylideneprost-5(Z),13(E)-dienoic acid; its sodium and potassium salts; and its methyl, ethyl, n-propyl and isopropyl esters.
(43) 6,9α-Methylene-11α,15α-dihydroxy-17-methyl-20-isopropylideneprost-5(E),13(E)-dienoic acid; its sodium and potassium salts, and its methyl, ethyl, n-propyl and isopropyl esters.
(44) 6,9α-Methylene-11α,15β-dihydroxy-17-methyl-20-isopropylideneprost-5(E),13(E)-dienoic acid; its sodium and potassium salts; and its methyl, ethyl, n-propyl and isopropyl esters.
(45) 6,9α-Methylene-11α,15α-dihydroxy-20-(1-ethylpropylidene)prost-5(Z),13(E)-dienoic acid; its sodium and potassium salts; and its methyl, ethyl, n-propyl and isopropyl esters.
(46) 6,9α-Methylene-11α,15β-dihydroxy-20-(1-ethylpropylidene)prost-5(Z),13(E)-dienoic acid; its sodium and potassium salts; and its methyl, ethyl, n-propyl and isopropyl esters.
(47) 6,9α-Methylene-11α,15α-dihydroxy-20-(1-ethylpropylidene)prost-5(E),13(E)-dienoic acid; its sodium and potassium salts; and its methyl, ethyl, n-propyl and isopropyl esters.
(48) 6,9α-Methylene-11α,15β-dihydroxy-20-(1-ethylpropylidene)prost-5(E),13(E)-dienoic acid; its sodium and potassium salts; and its methyl, ethyl, n-propyl and isopropyl esters.

Of these, the most preferred compounds are those acids numbered 1, 2, 3, 4, 21, 22, 23, 24, 25, 26, 27, 28, 37, 38, 39, 40, 41, 42, 43 and 44, and those sodium salts and methyl esters numbered 3, 39 and 43.

PHARMACOLOGICAL ACTIVITY

The prostacyclin derivatives of general formula (I) and their pharmacologically acceptable salts have shown excellent thrombocyte agglutination inhibitory, coronary blood vessel dilatory and bronchodilatory activity. Of these activities, the results of study on thrombocyte agglutination inhibition will be discussed in more detail below.

TEST METHOD

The inhibition of platelet aggregation was assessed by Born's turbidimetric method [Nature, 194, 927–929 (1962)].

Blood was collected from a male rat of the Sprague-Dawley strain (body weight 250–300 g). To the blood was added 3.8% of citric acid, and the mixture was centrifuged, to prepare a platelet-rich plasma. Platelet aggregation was determined by the following means, 0.05 ml of a test liquid (containing the compound whose inhibitory effect was to be tested) was added to 1 ml of this platelet-rich plasma, 2 minutes after the addition, 0.2 ml of a collagen-containing liquid (final concentration 100 μg/ml) or 0.2 ml of an adenosine diphosphate (ADP)-containing liquid (final concentration 5 μM) were added; the increase in light transmission at 600 nm was determined by means of a platelet aggregometer manufactured by Bryston Co Limited. The rate of inhibiting the increase in transparency at the time of addition of a test compound against that of the control was calculated and, from this, the concentration required for inhibiting aggregation by 50% was calculated. The following compounds were tested:

Compd. A; 6,9α-Methylene-11α,15α-dihydroxyprost-5(E),13(E)-dienoic acid
Compd. B; 6,9α-Methylene-11α,15α-dihydroxyprost-5(Z),13(E)-dienoic acid
Compd. C; 6,9α-Methylene-11α,15β-dihydroxyprost-5(E),13(E)-dienoic acid
Compd. D; 6,9α-Methylene-11α,15β-dihydroxyprost-5(Z),13(E)-dienoic acid
Compd. E; 6,9α-Methylene-11α,15α-dihydroxy-20-isopropylideneprost-5(Z),13(E)-dienoic acid
Compd. F; 6,9α-Methylene-11α,15α-dihydroxy-20-isopropylideneprost-5(E),13(E)-dienoic acid Compd. G; 6,9α-Methylene-11α,15β-dihydroxy-20-isopropylideneprost-5(E),13(E)-dienoic acid Compd. H; 6,9α-Methylene-11α,15α-dihydroxy-17R-methyl-20-isopropylideneprost-5(E),13(E)-dienoic acid (optical isomer I).

Also tested were the known PGE$_1$ and aspirin. The results are shown in the following Table.

| Test Compd | Concentration required to inhibit aggregation by 50% (g./ml). | |
|---|---|---|
| | Aggregation by Collagen | Aggregation by ADP |
| Compd A | $3.5 \times 10^{-8}$ | $6.5 \times 10^{-8}$ |
| Compd B | $4.5 \times 10^{-7}$ | $2.3 \times 10^{-6}$ |
| Compd C | $2.1 \times 10^{-6}$ | $2.3 \times 10^{-6}$ |
| Compd D | $3.1 \times 10^{-6}$ | $2.4 \times 10^{-5}$ |
| Compd E | $3.4 \times 10^{-7}$ | $1.9 \times 10^{-7}$ |
| Compd F | $1.9 \times 10^{-8}$ | $2.4 \times 10^{-8}$ |
| Compd G | $3.4 \times 10^{-7}$ | $1.1 \times 10^{-6}$ |
| Compd H | $2.2 \times 10^{-8}$ | $3.8 \times 10^{-8}$ |
| PGE$_1$ | $7.5 \times 10^{-8}$ | $9.4 \times 10^{-8}$ |
| Aspirin | $9.4 \times 10^{-6}$ | $6.0 \times 10^{-4}$ |

As can clearly be seen from the test results given above, compounds of general formula (I), and thus its pharmacologically salts, are useful for the treatment and prophylaxis of thrombosis. The compounds are preferably administered as pharmaceutical compositions in admixture with one or more diluents and or excipients. They may be administered, for example, orally (e.g. in the form of a tablet, capsule, granule, powder or syrup) or parenterally (e.g. by intravenous injection). Although the dosage will vary depending upon the symptoms, age and body weight of the patient, the compounds of the invention may be administered to an adult in a daily dosage of about 0.001 to 1,000 mg. preferably about 0.01 to 100 mg, in a single dose or in divided doses.

The compounds of formula (I) can be prepared by reacting a compound of formula (II):

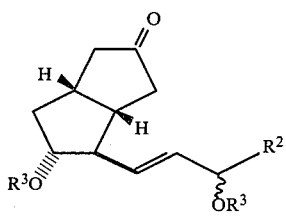

(II)

with a Wittig reagent of formula (III):

$(R^4)_3 P^{\oplus} - C^{\ominus} H - (CH_2)_n COOM$ (III)

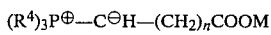

and then converting this product into a free acid by treatment with an acid. The product of this step is a compound of formula (I) in which $R^1$ represents a hydrogen atom, but in which the two hydroxy groups are protected by the group $R^3$. If required, this product may then be esterified, to convert the free acid to the desired ester ($R^1$ represents a lower alkyl group). At this stage, the product is a compound of formula (IV)

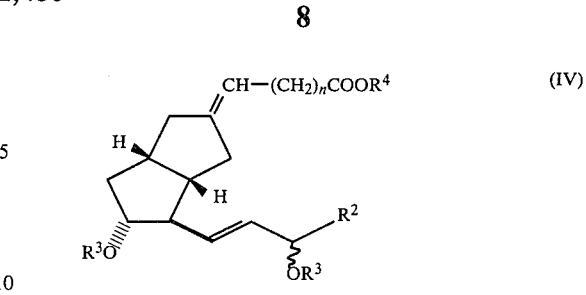

(IV)

Finally, the hydroxy-protecting groups are removed and, if desired, the ester may be hydrolized to the corresponding acid.

The definitions of $R^2$ and n have already been discussed in connection with the compounds of formula (I). $R^3$ represents a hydroxy-protecting group. There is no particular limitation upon the nature of this group, provided that it is not such that any other part of the compound is affected when the protecting group is replaced by a hydrogen atom. Examples of suitable protecting groups include: 5- or 6-membered heterocyclic groups having an oxygen or sulphur atom in the ring and which may be unsubstituted or have one or more alkoxy substitutents, for example 2-tetrahydrofuranyl, 2-tetrahydropyranyl, 4-methoxytetrahydropyran-4-yl, or 2-tetrahydrothiopyranyl; a lower alkyl group having one or more alkoxy and or aralkoxy substitutents, for example methoxymethyl, ethoxymethyl, 1-ethoxyethyl, or benzyloxymethyl; or a tri (lower alkyl) silyl group, for example trimethylsilyl, triethylsilyl or tri-n-propylsilyl.

$R^4$ represents an aryl group (e.g. phenyl) or an alkyl group (e.g. methyl or n-butyl). $R^1$ represents a hydrogen atom or a lower alkyl group, for example methyl, ethyl, n-propyl, isopropyl, n-butyl, isobutyl, n-pentyl or isopentyl. M represents an alkali metal atom, for example sodium, potassium or lithium.

The Wittig reaction, in which the compound of formula (II) is reacted with the Wittig reagent of formula (III) is preferably carried out in the presence of a solvent and preferably using from 1 to 20 moles of the Wittig reagent of formula (III) per mole of the compound of formula (II), more preferably using an excess of the Wittig reagent.

The solvent used for this reaction may be any solvent which can, in general, be used for Wittig reactions and there is no particular limitation, provided that it has no adverse effect upon the reaction. The solvent will be organic and suitable examples include: ethers, such as diethyl ether, tetrahydrofuran, dioxan or dimethoxyethane; thioethers, such as sulforane; hydrocarbons, such as benzene, toluene or xylene; dialkyl sulfoxides, such as dimethyl sulfoxide; aliphatic acid dialkylamides, such as dimethylformamide or dimethylacetamide; halogenated hydrocarbons, such as dichloromethane or chloroform; and phosphoric acid triamides, such as hexamethylphosphoric triamide (HMPA). The reaction is preferably carried out under a stream of an inert gas, for example nitrogen, argon or helium. While the reaction temperature is not particularly critical, we would normally conduct the reaction at a temperature of from $-10°$ C. to the reflux temperature of the solvent employed, preferably about room temperature. The time required for the reaction will vary, depending upon the reaction temperature, but it will normally be within the range from 6 to 24 hours. The product obtained by the Wittig reaction is a salt, which can easily be converted into a free acid by treatment with an acid, which may be organic (for example acetic acid, propionic acid or oxalic acid) or a mineral acid (for example hydrochloric acid or hydrobromic acid).

After completion of the Wittig reaction, the desired product may be recovered from the reaction medium by conventional means. For example, iced water can be added to the reaction mixture, the resulting mixture treated with acid (as mentioned above) and extracted with an organic solvent, such as diethyl ether, and then, after washing the organic phase with water and drying, the solvent may be distilled off from the organic phase, thus giving the desired product. If required, this product may then be esterified. The esterification may be carried out by contacting the product with an esterifying agent in the presence or absence of a solvent. There is no particular limitation upon the nature of the esterifying agent employed and, indeed, any such agent used for converting an ordinary carboxyl group to an alkoxycarbonyl group may be used. Examples of esterifying agents which can be used in this reaction include, for example: diazoalkanes, such as diazomethane, diazoethane, diazo-n-propane, diazoisopropane or diazo-n-butane; or a combination of an alcohol which forms an ester group (e.g. methanol, ethanol, n-propanol, isopropanol or n-butanol) with a mineral acid (e.g. hydrochloric acid, hydrobromic acid or sulphuric acid) or an organic acid (e.g. methanesulfonic acid, benzenesulfonic acid or p-toluenesulfonic acid). Where a diazoalkane is employed, the reaction is preferably carried out in the presence of a solvent, although there is no particular limitation upon the nature of the solvent, provided that it does not adversely affect the reaction. Ethers, such as diethyl ether or dioxan, are preferred solvents. The reaction temperature is not particularly critical but, where a diazoalkane is used, we prefer to carry out the esterification reaction under ice-cooling in order to suppress side reactions and to prevent decomposition of the diazoalkane. Where an alcohol plus an acid is employed as the esterifying agent, we prefer that an excess of the alcohol be used as the solvent. Again, the reaction temperature is not particularly critical, and we therefore prefer to carry out the reaction at a temperature between room temperature and the reflux temperature of the alcohol employed. The reaction time will vary, depending mainly upon the reaction temperature and the type of alcohol employed; usually, it will vary from 1 hour to 2 days.

After completion of the reaction, the ester obtained may be recovered from the reaction mixture by conventional means. One such method comprises: distilling off the solvent from the reaction mixture; dissolving the residue in an organic solvent; washing the solution with an aqueous alkaline solution (preferably an alkali metal carbonate or bicarbonate, such as sodium bicarbonate or sodium carbonate); drying the organic solution; and distilling off the organic solvent.

The reaction employed to remove the hydroxy-protecting group from the compound of formula (IV) thus obtained will depend largely upon the nature of the protecting group.

Where the protecting group is a heterocyclic group (e.g. 2-tetrahydropyranyl) or an alkoxy- or aralkoxy-substituted lower alkyl group (e.g. methoxymethyl or benzyloxymethyl), the reaction can easily be carried out by contacting the compound of formula (IV) with an acid. The acid used may be an organic acid (e.g. formic acid, acetic acid, propionic acid, butyric acid, oxalic acid or malonic acid) or a mineral acid (e.g. hydrochloric acid, hydrobromic acid or sulphuric acid). Although the reaction may be conducted in the presence or absence of a solvent, the reaction proceeds more smoothly in the presence of a solvent. The nature of the solvent is not particularly critical, provided that it has no adverse effect upon the reaction. Solvents preferably used include: water; alcohols, such as methanol or ethanol; ethers, such as tetrahydrofuran or dioxan; or a mixture of water with one or more of these organic solvents. The reaction temperature, also, is not particularly critical and we therefore prefer to conduct the reaction at a temperature from room temperature to the reflux temperature of the solvent (if employed) more preferably at about room temperature.

Where the hydroxy-protecting group is a tri(lower alkyl)silyl group, removal of the protecting group is best accomplished by contacting the compound of formula (IV) with water, optionally containing an acid or base. There is no particular limitation upon the nature of the acid or base and examples include: organic acids, such as formic acid, acetic acid, propionic acid, butyric acid, oxalic acid and malonic acid; mineral acids, such as hydrochloric acid, hydrobromic acid and sulphuric acid; alkali metal or alkaline earth metal hydroxides, such as potassium hydroxide or calcium hydroxide; and alkali metal or alkaline earth metal carbonates, such as potassium carbonate or calcium carbonate. When water is employed as a solvent, no other solvent is required for the reaction. If, however, another solvent than water is employed, it may be a mixture of water with an organic solvent, for example an ether (e.g. tetrahydrofuran or dioxan) or an alcohol (e.g. methanol or ethanol). The reaction temperature is not particularly critical and for this reason the reaction is preferably carried out at about room temperature.

After completion of the reaction, the product may be recovered from the reaction mixture by conventional means. An example of suitable method is as follows: the reaction mixture is neutralized; a suitable solvent is added thereto and the product extracted into the solvent; the extract is washed with water and dried; and then the solvent is distilled off from the extract leaving the desired product as the residue.

Where the product of the above reaction is an ester, the ester group may be removed by hydrolysis, if desired, by contacting the compound with an acid or a base in the presence of a solvent. There is no particular limitation on the nature of the acid or base used and any acid or base commonly used in hydrolysis reactions may be employed. The reaction is preferably carried out under basic conditions using an alkali metal or alkaline earth metal hydroxide e.g. lithium hydroxide, sodium hydroxide, potassium hydroxide, calcium hydroxide or barium hydroxide. There is also no particular limitation upon the nature of the solvent used, provided that it does not have any adverse effect upon the reaction. The solvent is preferably an organic solvent, for example: an alcohol, such as methanol, ethanol, n-propanol or isopropanol; or an ether, such as diethyl ether, tetrahydrofuran, dioxan or dimethoxyethane; or it may be a mixture of one or more of these organic solvents with water. Although the reaction temperature is not particularly critical, we normally prefer to carry out the reaction at a temperature from room temperature to the reflux temperature of the solvent employed. The time taken for the reaction is generally from 1 to 12 hours, although it will vary, depending upon the reaction temperature and other reaction conditions.

After completion of the hydrolysis reaction, the desired product may be recovered from the reaction mixture by conventional means. For example, one such method comprises: acidifying the reaction mixture; extracting the mixture with a suitable organic solvent; and distilling off the organic solvent, to leave the desired product behind as a residue.

Each of the compounds produced in the above reaction steps may be further purified, if necessary, by such conventional techniques as column chromatography, thin layer chromatography or recrystallization. In cases where the desied compound thus formed is obtained as a mixture of geometric or optical isomers, these isomers may be separated or resolved at an appropriate step in the synthesis.

PREPARATION OF INTERMEDIATES

Wittig reagent

The Wittig reagent of formula (III), which is used in the process of the present invention can be obtained by reacting a compound of formula (III'):

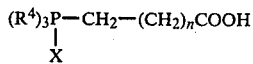

(in which $R^4$ and n are as defined above and X represents a halogen atom, e.g. chlorine or bromine) with an alkali metal base, for example: an alkali metal hydride, such as sodium hydride or potassium hydride; an alkali metal alkoxide, such as sodium methoxide, sodium ethoxide or potassium t-butoxide; an alkali metal amide, such as sodium amide or potassium amide; an alkylalkali metal, such as n-butyllithium; or an alkali metal dimethyl sulphoxide anion, such as sodium dimethyl sulphoxide anion. The solvent used for this reaction may be any one of those exemplified for the reaction of the Wittig reagent with compound (II).

Preparation of Compound (II)

Method A

The compound of formula (II), which is used as the other starting material in the process of the invention is a novel compound and may be prepared, for example, by the procedure summarized in the following reaction scheme:

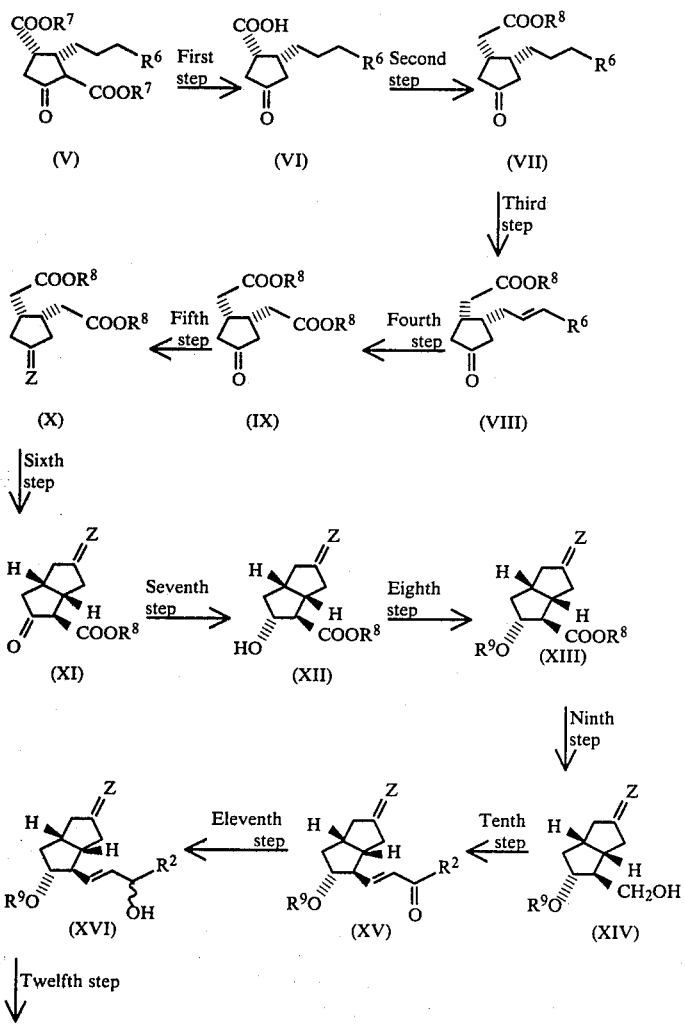

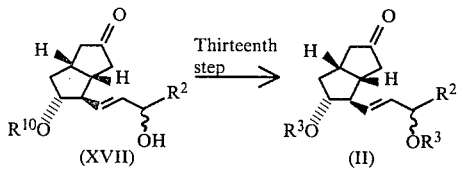

In the above formulae, $R^2$ and $R^3$ are as defined above; $R^6$ represents an aryl group (such as phenyl); $R^7$ and $R^8$ are the same or different and each represents a lower alkyl group (such as methyl, ethyl, n-propyl, isopropyl, n-butyl or isobutyl); $R^9$ has the same meaning as defined for $R^3$, that is a hydroxy-protecting group; $R^{10}$ represents a hydrogen atom or the same group as defined for $R^3$, that is a hydroxy-protecting group; and Z represents a carbonyl-protecting group. There is no particular limitation upon the nature of the carbonyl-protecting group represented by Z, provided that other parts of the compound are not affected when the protecting group is removed. Examples of such protecting groups include: dialkoxy groups, such as dimethoxy or diethoxy; alkylenedioxy groups, such as methylenedioxy or ethylenedioxy; and alkylenedithio groups, such as ethylenedithio or trimethylenedithio.

This reaction scheme uses as a starting material a compound of formula (V), which may be prepared by the method described on page 101 of Tetrahedron Letters (1976).

The first step in this reaction scheme produces a compound of formula (VI) by hydrolysis of a compound of formula (V) and subsequent decarboxylation of the product. These two reactions may be conducted by a standard method by heating compound (V) under reflux with a mixture of mineral and organic acids. Examples of suitable mineral acids are dilute hydrochloric acid, dilute sulphuric acid or dilute perchloric acid and examples of suitable organic acids are acetic acid or propionic acid.

The second step consists of treating the compound of formula (VI) with a halogenating agent to produce an acid halide of formula (XVIII):

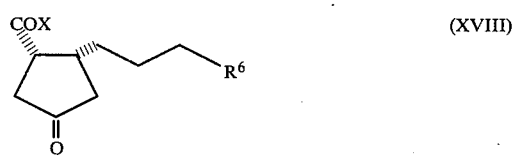

(in which $R^6$ is as defined above and X represents a halogen atom, e.g. chlorine or bromine), reacting the halide (XVIII) with diazomethane dissolved in ether to produce a diazoketone derivative of formula (XIX):

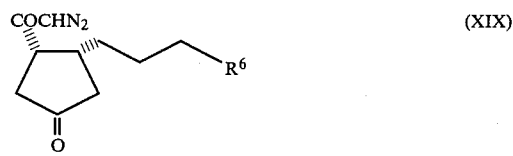

and then subjecting the diazoketone derivative (XIX) to a Wolff rearrangement in the presence of an alcohol. The reaction involved in this, the second, step is known as an Arndt-Eistert reaction and can be carried out without isolating intermediate compounds (XVIII) and (XIX). The halogenating agent which is used in the first part of this step may be, for example, oxalyl chloride, thionyl chloride, phosphorus oxychloride, phosphorus pentachloride or phosphorus pentabromide. There is no particular limitation upon the nature of the alcohol used in the Wolff rearrangement of diazoketone derivative (XIX), provided that it can form an ester group in the desired compound (VII) and examples of suitable alcohols include, for example, methanol, ethanol, n-propanol, isopropanol, n-butanol and isobutanol. The Wolff rearrangement reaction is preferably carried out in the presence of a metal catalyst or of light. Examples of suitable metal catalysts include, for example: silver salts or other silver compounds, such as silver nitrate, silver oxide, silver acetate or silver benzoate; and copper salts, such as copper sulphate or copper acetate.

The third step in this process consists of the preparation of a compound of formula (VIII) by reacting the compound of formula (VII) with a brominating agent to produce a brominated compound of formula (XX):

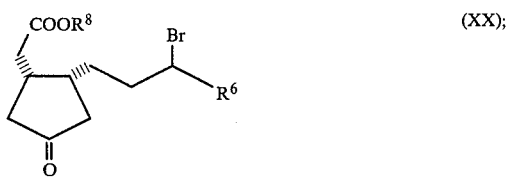

reacting compound (XX) with selenophenol or phenylmercaptan; and then oxidizing the seleno or mercapto compound thus obtained. Alternatively, the brominated compound (XX) may be simply treated with a base. Examples of suitable brominating agents include N-bromo acid amides, such as N-bromoacetamide or N-bromosuccinimide. Examples of oxidizing agents used to oxidize the seleno or mercapto compound include aqueous hydrogen peroxide, peracetic acid, m-chloroperbenzoic acid, t-butyl hydroperoxide and sodium metaperiodate. Examples of bases which may be used to treat the brominated compound (XX) include any conventional dehydrohalogenating agent, although we prefer to use organic bases, such as 1,5-diazabicyclo[4.3.0]nonene-5(DBN) or 1,8-diazabicyclo[5.4.0]undecene-7(DBU).

The fourth step consists in the preparation of a compound of formula (IX) by subjecting the compound of formula (VIII) to oxidative splitting to form an aldehyde of formula (XXI):

oxidizing the aldehyde (XXI) to a carboxylic acid of formula (XXII):

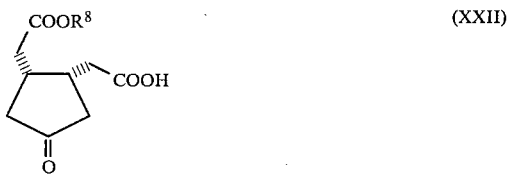
(XXII)

and then esterifying the carboxylic acid (XXII) by a conventional method. The entire sequence of reactions may be carried out without intermediate isolation or purification of the intermediates (XXI) and (XXII). The oxidizing agent used in the oxidative splitting to form aldehyde (XXI) is preferably sodium metaperiodate or osmium tetraoxide. The oxidizing agent used to form the carboxylic acid (XXII) is preferably: a chromate, such as chromic anhydride, sodium dichromate or potassium dichromate; potassium permanganate; or silver oxide. The esterification of the carboxylic acid (XXII) to the desired compound (IX) may be effected by treatment with an esterifying agent under conditions conventionally used for esterification reactions; these conditions are similar to those used in the esterification reactions which may form part of the process of the present invention.

The fifth step involves the preparation of the compound of formula (X) by protecting the carbonyl group of the compound of formula (IX). The nature of this reaction will depend upon the particular carbonyl-protecting group chosen, as will be well understood by those skilled in the art. Normally, it will simply consist in contacting the compound (IX) with a compound capable of forming the desired protecting group. Examples of such compounds include: orthoformic acid esters which form ketals, such as methyl orthoformate or ethyl orthoformate; alkylene glycols, which form cyclic ketals, such as methylene glycol or ethylene glycol; and alkylene dithioglycols which form cyclic thioketals, such as ethylene dithioglycol or trimethylene dithioglycol.

The sixth step of this process subjects the compound of formula (X) to a Dieckmann condensation reaction to prepare a compound of formula (XI). This reaction is carried out using a base in the presence of an inert solvent under conventional conditions. Suitable bases include: alkali metal alkoxides, such as sodium methoxide or potassium t-butoxide; or alkali metal hydrides, such as sodium hydride or potassium hydride.

The seventh step consists in reducing the compound of formula (XI) to a compound of formula (XII). There is no particular limitation upon the nature of the reducing agent employed, provided that it converts only a carbonyl group into a hydroxy group. Preferred reducing agents are various metal hydrides, for example sodium borohydride, potassium borohydride, lithium borohydride, zinc borohydrate, lithium tri-t-butoxyaluminium hydride, lithium trimethoxyaluminium hydride or sodium cyanoborohydride.

The eighth step of this process consists in protecting the hydroxy group of the compound of formula (XII), to give the compound of formula (XIII). This reaction is carried out by conventional means, simply by contacting the compound of formula (XII) with a compound capable of forming a hydroxy-protecting group. Examples of such compounds include: heterocyclic compounds, such as dihydropyran, dihydrothiopyran, dihydrothiophene and 4-methoxy-5,6-dihydro-(2H)-pyran; alkoxy- or aralkoxy-substituted alkyl halides, such as methoxymethyl chloride, ethoxyethyl chloride or benzyloxymethyl chloride; unsaturated ethers, such as methyl vinyl ether or ethyl vinyl ether; or silyl compounds, such as hexamethyldisilazane or trimethylsilyl chloride. Where a heterocyclic compound or an unsaturated ether is used, the reaction is preferably conducted in the presence of a small amount of an acid, which may be a mineral acid (e.g. hydrochloric acid or hydrobromic acid) or an organic acid (such as picric acid, trifluoroacetic acid, benzenesulphonic acid or p-toluenesulphonic acid). Where an alkoxy- or aralkoxy-substituted alkyl halide or a vinyl compound is used, the reaction is preferably conducted in the presence of a base.

The ninth step consists in the reduction of the compound of formula (XIII) to a compound of formula (XIV). This reaction is usually conducted using a reducing agent in the presence of a solvent. Preferred reducing agents are metal hydrides, such as lithium aluminium hydride, sodium borohydride, potassium borohydride, lithium borohydride, zinc borohydride, lithium tri-t-butoxyaluminium hydride or lithium trimethoxyaluminium hydride.

The tenth step involves the preparation of a compound of formula (XV) by oxidizing a compound of formula (XIV) to a compound of formula (XXIII):

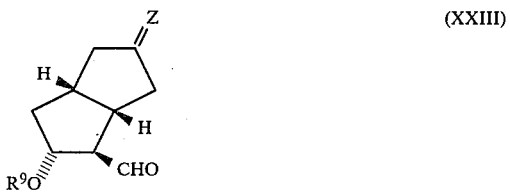
(XXIII)

and then reacting this compound (XXIII) with a Wittig reagent of formula (XXIV):

(XXIV)

or with a modified Wittig reagent of formula (XXV):

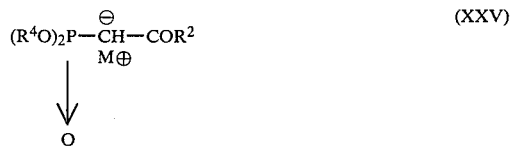
(XXV)

Preferred oxidizing agents used to prepare the compound of formula (XXIII) include: chromates, such as chromic anhydride, chromic anhydride-pyridine complex (Collins' reagent), chromic anhydride-concentrated sulphuric acid-water (Jones' reagent), sodium dichromate or potassium dichromate; an organic active halogen compound, such as N-bromoacetamide, N-bromoasuccinimide, N-bromophthalimide, N-chloro-p-toluenesulphonamide or N-chlorobenzene sulphonamide; an aluminium alkoxide, such as aluminium t-butoxide or aluminium isopropoxide; or dimethyl sulphoxide-dicyclocarbodiimide. The aldehyde (XXIII) thus obtained can usually be reacted, without purification, with the Wittig reagent (XXIV) or modified Wittig reagent (XXV) and the reaction conditions are similar to those employed in the process of the invention when reacting compound (II) with the Wittig reagent (III).

The eleventh step of the process of the invention consists in the reduction of a compound of formula (XV) to a compound of formula (XVI). The reaction conditions employed in this step are similar to those employed, as described above, in the seventh step.

The twelfth step of this process involves preparing a compound of formula (XVII), and may be accomplished by removing the carbonyl-protecting group from the compound of formula (XVI). The nature of this reaction depends upon the nature of the carbonyl-protecting group which is to be removed. Where the protecting group is a dialkoxy group (e.g. dimethoxy or diethoxy) or an alkylene dioxy group (e.g. methylene dioxy or ethylene dioxy), it may be removed by contacting the compound of formula (XVI) with a mixture of an acid and an aqueous solvent, e.g. acetic acid/water, dilute hydrochloric acid/aqueous acetone, dilute hydrochloric acid/aqueous acetonitrile or dilute sulphuric acid/aqueous acetone. Such a reaction will normally simultaneously remove the hydroxy-protecting group.

Where the carbonyl-protecting group is an alkylenedithio group (e.g. an ethlenedithio or trimethylenedithio group), it may be removed by contacting the compound with mercuric chloride in the presence of a solvent.

The thirteenth step in this process consists in protecting the hydroxy group of the compound of formula (XVII) to produce a compound of formula (II). The conditions employed for this step are generally similar to the conditions employed in the eighth step of this process.

In the steps mentioned above, each of the desired compounds can be separated from the reaction mixture by conventional means, at the end of each reaction and, if desired, the compounds obtained may be further purified by conventional methods, e.g. column chromatography or thin layer chromatography. Moreover, where the compound obtained comprises a mixture of various geometrical or optical isomers, these isomers may be used in admixture or may be separated by conventional means prior to a subsequent step.

Method B

An alternative method of preparing the compounds of formula (II) used as starting materials in the process of the invention consists of the preparation of a compound of formula (IX) or (X), as defined above, by oxidizing a compound of formula (XXX)

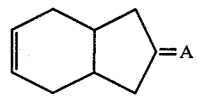
(XXX)

(in which A represents an oxo group or a carbonyl-protecting group) and then, if necessary, esterifying the carboxylic acid thus obtained. The compound thus obtained is a compound of formula (XXXI):

(XXXI)

(in which $R^a$ represents a hydroxy group or a lower alkoxy group and A is as defined above).

In the compound of formula (XXXI), $R^a$ may represent a hydroxy group or an alkoxy group; where it represents an alkoxy group, this may be straight or branched chain and preferably having from 1 to 4 carbon atoms; examples include methoxy, ethoxy, n-propoxy, isopropoxy, n-butoxy and isobutoxy groups. A represents an oxo group or a carbonyl-protecting group, for example a dialkoxy group (e.g. dimethoxy or diethoxy), an alkylenedioxy group (e.g. ethylenedioxy) or an alkylenedithio group (e.g. ethylenedithio or trimethylenedithio).

The oxidation of the compound of formula (XXX) can be carried out using any oxidizing agent capable of splitting the carbon-carbon double bond to form aldehyde groups and optionally capable of oxidizing these aldehyde groups further to carboxylic acid groups. Certain oxidizing agents are capable of carrying out both the oxidative splitting of the carbon-carbon double bond and the oxidation of the resulting aldehyde groups to carboxylic acid groups. Other oxidizing agents are capable only of the oxidative splitting of the carbon-carbon double bond to form aldehyde groups and it is then necessary to use other oxidizing agents to convert these aldehyde groups into carboxylic groups. Examples of oxidizing agents which may be used for the oxidative splitting of the carbon-carbon double bond to form aldehyde groups are sodium metaperiodate, osmium tetraoxide; ozone and zinc/acetic acid. Examples of oxidizing agents which may be used to convert the aldehyde groups in the compound thus obtained (usually without any intermediate isolation of the aldehyde compound) to carboxylic acid groups include, for example, chromates [e.g. chronic anhydride/concentrated sulphuric acid/water (Jones' reagent), sodium dichromate or potassium dichromate], permanganates (e.g. sodium permanganate or potassium permanganate and silver oxide). Examples of oxidizing agents which may be used to convert the compound of formula (XXX) directly to the desired carboxylic acid compound of formula (XXXI) include: a combination of ozone and hydrogen peroxide; a combination of sodium periodate and potassium permanganate; and a combination of sodium metaperiodate and ruthenium tetraoxide. There is no particular limitation upon the nature of the solvent used in this oxidation reaction, provided that it has no adverse effect upon the reaction. Examples of suitable solvents include: water; ethers, such as tetrahydrofuran or dioxan; ketones, such as acetone or methylethyl ketone; tertiary alcohols, such as t-butanol, aliphatic hydrocarbons, such as n-hexane; halogenated hydrocarbons, such as methylene chloride, chloroform or carbon tetrachloride; organic acids, such as acetic acid; or a mixture of water and one or more of these organic solvents soluble in water. The reaction temperature, also, is not particularly critical, but relatively low temperatures are preferred, in order to reduce side reactions. Usually, we prefer to carry out the reaction at a temperature from −10° C. to room temperature. Although the time required for the reaction will depend upon the type of oxidizing agent to be used and the reaction temperature, generally the reaction will take from 1 to 15 hours.

After completion of the reaction, the product may be recovered from the reaction mixture by conventional means. An example of one such technique comprises: adding an organic solvent to the reaction mixture; washing the organic phase with water; drying the washed organic phase; and finally distilling off the organic solvent.

It is then desirable to esterify the carboxylic acid groups on the compound thus obtained. This esterification reaction may be carried out in the presence or absence of a solvent. Reaction conditions, solvents and esterifying agents which may be used in this esterification are the same as the reaction conditions, solvents and esterifying agents described in relation to the esterification reaction forming part of the process of the invention. If desired, the compound thus produced may be separated from the reaction mixture and details of how this may be achieved are also given in relation to the esterification reaction forming part of the process of the invention.

The compound of formula (XXX) is also a novel compound and this may be prepared, for example, by the procedure summarized in the following reaction scheme.

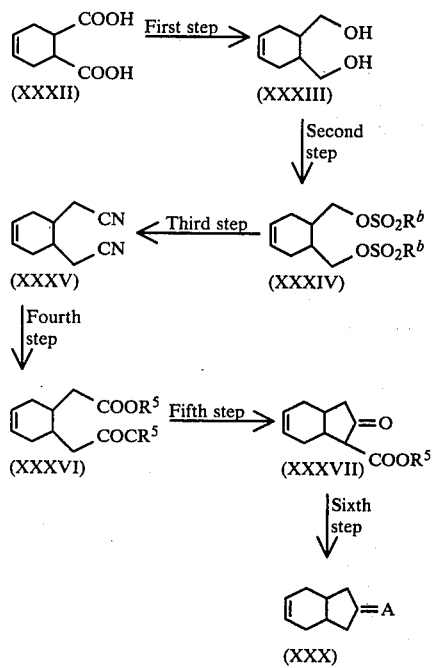

In the formulae given above A has the meaning already defined; $R^b$ represents a lower alkyl group (e.g. methyl, ethyl, n-propyl or isopropyl) or an aryl group (e.g. phenyl or p-tolyl); and $R^5$ represents a lower alkyl group (e.g. methyl, ethyl, n-propyl or isopropyl).

The first step in this reaction scheme involves preparing a compound of formula (XXXIII) by reducing a compound of formula (XXXII). This reaction may be carried out by contacting the compound of formula (XXXII) with a reducing agent in the presence of a solvent. Preferred reducing agents are alkali metal aluminium hydrides, such as lithium aluminium hydride. The solvent is preferably an ether, such as diethyl ether or tetrahydrofuran.

The second step in this reaction scheme consists in reacting the compound of formula (XXXIII) with a sulphonyl halide of formula $R^bSO_2X$ (in which $R^b$ is as defined above and X represents a halogen atom, e.g. chlorine or bromine) to prepare a compound of formula (XXXIV). Suitable sulphonyl halides include, for example, methanesulphonyl chloride and p-toluenesulphonyl chloride. The reaction is preferably effected in the presence of a base, for example triethylamine, pyridine or 2,6-lutidine.

The third step in this reaction scheme consists in contacting the compound of formula (XXXIV) with an alkali metal cyanide in the presence of a solvent. The alkali metal cyanide is preferably sodium cyanide or potassium cyanide. There is no particular limitation upon the nature of the solvent and examples include: water; alcohols such as methanol or ethanol; ketones such as acetone or methyl ethyl ketone; dialkyl aliphatic acid amides such as dimethylformamide or dimethylacetamide; dialkyl sulphoxides, such as dimethyl sulphoxide; or phosphoric acid triamides, such as HMPA; alternatively, there may be used a mixture of water with one or more of these organic solvents.

In the fourth step, the compound of formula (XXXV) prepared in the third step is alcoholized by contacting it with an alcohol of formula $R^5OH$, in the presence of an acid. The acid is preferably a mineral acid, such as hydrochloric acid, hydrobromic acid or sulphuric acid.

In the fifth step, the compound of formula (XXXVI) prepared in the fourth step is subjected to a Dieckmann condensation. This may be carried out by conventional means using a base in the presence of an inert solvent. Suitable bases include: alkali metal alkoxides, such as sodium methoxide, sodium ethoxide or potassium t-butoxide; or alkali metal hydrides, such as sodium hydride or potassium hydride. Suitable inert solvents are: armoatic hydrocarbons, such as benzene, toluene or xylene; dialkyl aliphatic acid amides, such as dimethylformamide or dimethylacetamide; dialkyl sulphoxides, such as dimethyl sulphoxide; and phosphoric acid triamides such as HMPA.

The sixth, and final, step in this reaction scheme consists of subjecting the compound of formula (XXXVII) produced in the fifth step to hydrolysis and decarboxylation and then, if required, protecting the carbonyl group of the compound thus obtained.

The initial hydrolysis and decarboxylation may be carried out by heating the compound of formula (XXXVII) under reflux with a mixture of a mineral acid and an organic acid, as is well-known in the art. Suitable mineral acids are dilute hydrochloric acid, dilute sulphuric acid or dilute perchloric acid and suitable organic acids are acetic acid or propionic acid.

The carbonyl group in the resulting compound of formula (XXXX):

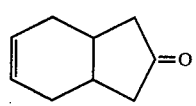

(XXXX)

maybe protected by means well-known in the art. Compounds which may be used to form the protecting group include: orthoformic acid esters which form ketals, such as methylorthoformate or ethyl orthoformate; alkylene glycols which form cyclic ketals, such as ethylene glycol; and alkylene thioglycols which form cyclic thio ketals, such as ethylenedithio glycol or trimethylenedithio glycol.

In each of these steps, the desired compounds may be separated from the reaction mixtures by treating the reaction mixtures by conventional means after completion of the reaction. If desired, the compounds thus obtained may be further purified by standard techniques, e.g. column chromatography or thin layer chromatography.

The prostacyclin compounds of the present invention may then be prepared by using the compound of formula (XXXI) thus obtained in place of the compound of formula (IX) or (X) in the procedure described as Method A.

The invention is further illustrated by the following Examples and Preparations. Preparations 1 to 23 illustrate Method A, whilst the remaining Preparations illustrate Method B.

EXAMPLE 1

Methyl ester of 6,9α-methylene-11α,15α-di-(2-tetrahydropyranyloxy)-prost-5,13(E)-dienoic acid

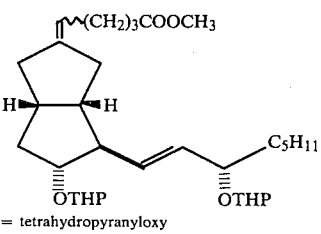

OTHP = tetrahydropyranyloxy

To 996 mg. of 3α-(2-tetrahydropyranyloxy)-4β-[3′α-(2″-tetrahydropyranyloxy)-1′-octenyl]-7-oxobicyclo[3.3.0]octane was added a ylide solution prepared from 17.9 g. of triphenylphosphine-ε-carboxybutyl bromide and a solution of dimethyl sulphoxide anion (prepared from 3.63 g. of a 55% solution of sodium hydride in oil and 200 ml. of dimethyl sulphoxide) in dimethyl sulphoxide; the resulting solution was allowed to stand overnight at room temperature under an atmosphere of argon. Thereafter, ice-water and then acetic acid were added thereto, and the resulting mixture was extracted with diethyl ether. The ethereal extract was washed with water and dried over anhydrous sodium sulphate, and then the solvent was removed by distillation. The residue thus obtained was esterified with a solution of diazomethane in diethyl ether, and then purified by silica gel column chromatography to give 1.165 g. of the desired product as an oil.

Infrared absorption spectrum (liquid film) $\nu_{max}$ cm$^{-1}$: 1740.

Nuclear magnetic resonance spectrum (CDCl$_3$) δppm: 0.90(3H, triplet); 3.66(3H, singlet); 4.70(2H, multiplet); 5.40(3H, multiplet).

EXAMPLE 2

Methyl ester of 6,9α-methylene-11α,15β-di(2-tetrahydropyranyloxy)-prost-5,13(E)-dienoic acid

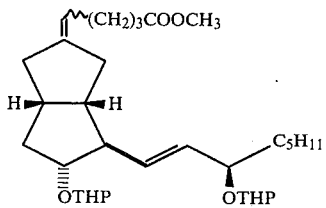

Reaction with a yield solution and subsequent treatment of the reaction mixture was conducted in the same manner as in Example 1, but using 1.247 g. of 3α-(2-tetrahydropyranyloxy)-4β-[3′β-(2″-tetrahydropyranyloxy)-1′-octenyl]-7-oxobicyclo[3.3.0]-octane to obtain 1.460 g. of the desired product as an oil.

Infrared absoprtion spectrum (liquid film) $\nu_{max}$ cm$^{-1}$: 1740.

Nuclear magnetic resonance spectrum (CDCl$_3$) δppm: 0.90(3H, triplet); 3.70(3H, singlet); 4.74(2H, multiplet); 5.40(3H, multiplet).

EXAMPLE 3

Methyl ester of 6,9α-methylene-11α,15α-dihydroxyprost-5,13(E)-dienoic acid

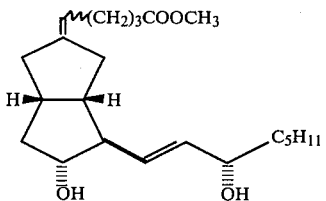

To 40 ml. of solution of 1.165 g. of methyl 6,9α-methylene-11α,15α-di(2-tetrahydropyranyloxy)-prost-5,13(E)-dienoate in acetic acid, there were added 20 ml. of water and 10 ml. of tetrahydrofuran, and the resulting mixture was allowed to stand overnight at room temperature. A saturated aqueous solution of sodium chloride was then added and the resulting mixture was extracted with ethyl acetate. After the extract had been washed with water and dried, the solvent was removed by distillation. The residue thus obtained was purified by silica gel column chromatography to give 376 mg. of the desired compound.

Infrared absorption spectrum (liquid film) $\nu_{max}$ cm$^{-1}$: 1735, 3350.

Nuclear magnetic resonance spectrum (CDCl$_3$) δppm: 3.75(3H, singlet); 5.22(1H, triplet); 5.45(2H, multiplet).

EXAMPLE 4

Methyl ester of 6,9α-methylene-11α,15β-dihydroxyprost-5,13(E)-dienoic acid

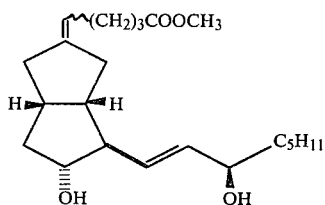

Reaction with acetic acid solution and subsequent treatment of the reaction mixture were conducted in the same manner as in Example 3, but using 1.140 g. of the methyl ester of 6,9α-methylene-11α,15β-di(2-tetrahydropyranyloxy)-prost-5,13(E)-dienoic acid, to give 518 mg. of the desired compound as an oil.

Infrared absorption spectrum (liquid film) $\nu_{max}$ cm$^{-1}$: 1740, 3370.

Nuclear magnetic resonance spectrum (CDCl$_3$) δppm: 3.68(3H, singlet); 5.24(1H, triplet); 5.62(2H, multiplet).

EXAMPLE 5

6,9α-Methylene-11α,15α-dihydroxyprost-5(E),13(E)-dienoic acid and
6,9α-methylene-11α,15α-dihydroxyprost-5(Z),13(E)-dienoic acid

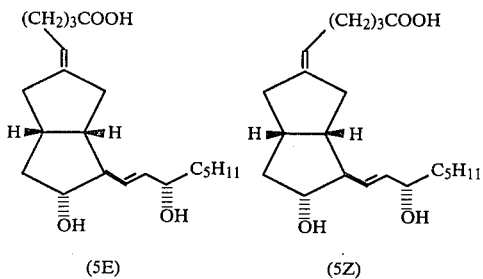

(5E)            (5Z)

A mixture of 200 mg. of methyl 6,9α-methylene-11α,15α-dihydroxyprost-5,13(E)-dienoate and 10 ml. of a 5% solution of potassium hydroxide in aqueous methanol (water:methanol=3:7 V/V) was stirred at room temperature for 4.5 hours. After completion of the reaction, the reaction mixture was acidified with acetic acid. A saturated aqueous solution of sodium chloric was then added, and the resulting mixture was extracted with ethyl acetate. After the extract had been washed with water and dried, the solvent was removed by distillation. The residue thus obtained was purified by silica gel thin layer chromatography. From the less polar fractions were obtained 35 mg. of a crystalline compound (the desired 5Z isomer). This was recrystallized from a mixed solvent comprising ethyl acetate and hexane in a volume ratio of 3:7, to give crystals melting at 89°–91° C. From the more polar fractions were obtained 123 mg. of the desired product as a crystalline compound (5E isomer). On recrystallization from a mixed solvent comprising ethyl acetate and hexane in a volume ration of 3:7, crystals melting at 68°–69° C. were obtained.

5Z isomer:

Infrared absorption spectrum (melted film) $\nu_{max}$ cm$^{-1}$: 1710, 3350.

Nuclear magnetic resonance spectrum (CDCl$_3$) δppm: 0.97(3H, triplet); 3.70(1H, multiplet); 4.05(1H, multiplet); 5.25(1H, multiplet); 5.53(2H, multiplet).

5E isomer:

Infrared absorption spectrum (melted film) $\nu_{max}$ cm$^{-1}$: 1710, 3350.

Nuclear magnetic resonance spectrum (CDCl$_3$) δppm: 0.89(3H, triplet); 3.70(1H, multiplet); 4.05(1H, multiplet); 5.28(1H, multiplet); 5.55(2H, multiplet).

EXAMPLE 6

6,9α-Methylene-11α,15β-dihydroxyprost-5(E),13(E)-dienoic acid and
6,9α-methylene-11α,15β-dihydroxyprost-5(Z),13(E)-dienoic acid

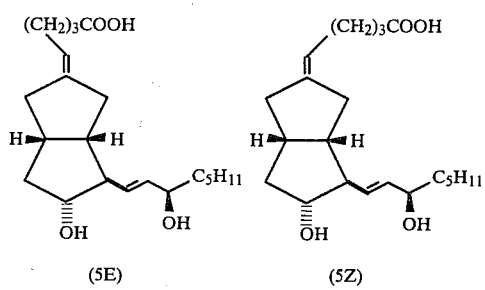

(5E)            (5Z)

An hydrolysis reaction and subsequent treatment of the reaction mixture were conducted in the same manner as in Example 5, but using 518 mg. of the methyl ester of 6,9α-methylene-11α,15β-dihydroxyprost-5,13(E)-dienoic acid, to give 142 mg. of the desired compound as an oil (5Z isomer) from the less polar fractions and 379 mg. of an oily compound (5E isomer) from the more polar fractions.

5Z isomer:

Infrared absorption spectrum (liquid film) $\nu_{max}$ cm$^{-1}$: 1710, 3350.

Nuclear magnetic resonance spectrum (CDCl$_3$) δppm: 0.89(3H, triplet); 3.70(1H, multiplet); 4.10(1H, multiplet); 5.30(1H, multiplet); 5.65(2H, multiplet).

5E isomer:

Infrared absorption spectrum (liquid film) $\nu_{max}$ cm$^{-1}$: 1710, 3350.

Nuclear magnetic resonance spectrum (CDCl$_3$) δppm: 0.89(3H, triplet); 3.70(1H, multiplet); 4.10(1H, multiplet); 5.30(1H, multiplet); 5.65(2H, multiplet).

EXAMPLE 7

Methyl ester of 6,9α-methylene-11α,15α-di(2-tetrahydropyranyloxy)-20-isopropylideneprost-5,13(E)-dienoic acid Reaction with a ylide solution and subsequent treatment of the reaction mixture were conducted in the same manner as in Example 1, but using 1.25 g. of 3α-(2-tetrahydropyranyloxy)-4β-[3α'-(2''-tetrahydropyranyloxy)-9'-methyl-1',8'-decadienyl]-7-oxobicyclo[3.3.0]octane, to give 978 mg. of the desired compound as an oil.

Infrared absorption spectrum (liquid film) $\nu_{max}$ cm$^{-1}$: 1745.

Nuclear magnetic resonance spectrum (CDCl$_3$) δppm: 3.31(3H, singlet); 4.68(2H, multiplet); 5.10(2H, multiplet); 5.50(2H, multiplet).

EXAMPLE 8

Methyl ester of 6,9α-methylene-11α,15β-di(2-tetrahydropyranyloxy)-20-isopropylideneprost-5,13(E)-dienoic acid Reaction with a ylide solution and subsequent treatment of the reaction mixture were conducted in the same manner as in Example 1, but using 1.25 g. of 3α-(2-tetrahydropyranyloxy)-4β-[3′β-(2″-tetrahydropyranyloxy)-9′-methyl-1′,8′-decadienyl]-7-oxobicyclo[3.3.0]octane, to give 756 mg. of the desired compound as an oil.

Infrared absorption spectrum (liquid film) $\nu_{max}$ cm$^{-1}$: 1745,

Nuclear magnetic resonance spectrum (CDCl$_3$) δppm: 3.31(3H, singlet); 4.68(2H, multiplet); 5.10(2H, multiplet); 5.60(2H, multiplet).

EXAMPLE 9

Methyl ester of 6,9α-methylene-11α,15α-dihydroxy-20-isopropylideneprost-5,13(E)-dienoic acid Reaction with an acetic acid solution and subsequent treatment of the reaction mixture were conducted in the same manner as in Example 3, but using 970 mg. of the methyl ester of 6,9α-methylene-11α,15α-dihydroxy-20-isopropylidene-prost-5,13(E)-dienoic acid, to give the desired compound as an oil.

Infrared absorption spectrum (liquid film) $\nu_{max}$ cm$^{-1}$: 3380, 1740.

Nuclear magnetic resonance spectrum (CDCl$_3$) δ ppm: 1.59(3H, singlet); 1.68(3H, singlet); 3.65(3H, singlet); 5.10(2H, multiplet); 5.49(2H, multiplet).

EXAMPLE 10

Methyl ester of 6,9α-methylene-11α,15β-dihydroxy-20-isopropylideneprost-5,13(E)-dienoic acid.

Reaction with an acetic acid solution and subsequent treatment of the reaction mixture were conducted in the same manner as in Example 3, but using 470 mg. of the methyl ester of 6,9α-methylene-11α,15β-di(2-tetrahydropyranyloxy)-20-isopropylideneprost-5,13(E)-dienoic acid, to give the desired compound as an oil.

Infrared absorption spectrum (liquid film) $\nu_{max}$ cm$^{-1}$: 3350, 1740

Nuclear magnetic resonance spectrum (CDCl$_3$) δ ppm; 1.60(3H, singlet); 1.68(3H, singlet); 3.65(3H, singlet); 5.20(2H, multiplet); 5.62(2H, multiplet).

EXAMPLE 11

6,9α-Methylene-11α,15α-dihydroxy-20-isopropylideneprost-5(E), 13(E)-dienoic acid and 6,9α-methylene-11α,15α-dihydroxy-20-isopropylideneprost-5(Z),13(E)-dienoic acid An hydrolysis reaction and subsequent treatment of the reaction mixture were conducted in the same manner as in Example 5, but using 591 mg. of the methyl ester of 6,9α-methylene-11α,15α-dihydroxy-20-isopropylideneprost-5,13(E)-dienoic acid, to give an oil (5Z isomer) from the less polar fractions and another oil (5E isomer) from the more polar fractions. The 5E isomer crystallized and had a melting point of 66°–67° C.

5Z isomer:

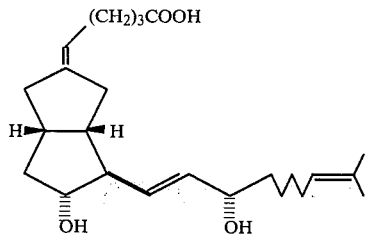

Infrared absorption spectrum (liquid film) $\nu_{max}$ cm$^{-1}$: 3450,1710,965.

Nuclear magnetic resonance spectrum (CDCl$_3$) δ ppm: 1.60(3H, singlet); 1.68(3H, singlet); 3.85(2H, multiplet); 5.22(2H, multiplet); 5.55(2H, multiplet).

5E isomer:

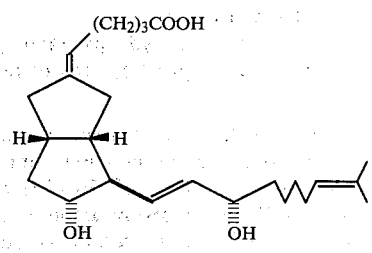

Infrared absorption spectrum (liquid film) $\nu_{max}$ cm$^{-1}$: 3450, 1710, 965.

Nuclear magnetic resonance spectrum (CDCl$_3$) δ ppm: 1.60(3H, singlet); 1.68(3H, singlet); 3.85(2H, multiplet); 5.22(2H, multiplet); 5.55(2H, multiplet).

EXAMPLE 12

6,9α-Methylene-11α,15β-dihydroxy-20-isopropylideneprost-5(E),13(E)-dienoic acid and 6,9α-methylene-11α,15β-dihydroxy-20-isopropylideneprost-5(Z),13(E)-dienoic acid An hydrolysis reaction and subsequent treatment of the reaction mixture were conducted in the same manner as in Example 5, but using 591 mg. of the methyl ester of 6,9α-methylene-11α,15β-dihydroxy-20-isopropylideneprost-5,15(E)-dienoic acid, to give an oily compound (5Z isomer) from the less polar fractions and another oily compound (5E isomer) from the more polar fractions.

5Z isomer:

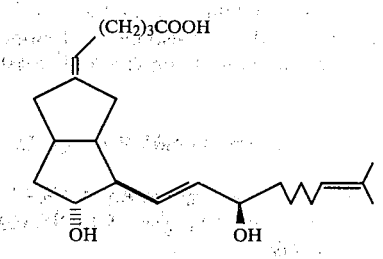

Infrared absorption spectrum (liquid film) $\nu_{max}$ cm$^{-1}$: 3450, 1710, 965.

Nuclear magnetic resonance spectrum (CDCl$_3$) δ ppm: 1.60(3H, singlet); 1.70(3H, singlet); 3.92(2H, multiplet); 5.33(2H, multiplet); 5.63(2H, multiplet).

5E isomer:

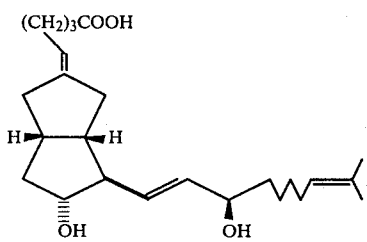

Infrared absorption spectrum (liquid film) $\nu_{max}$ cm$^{-1}$: 3450, 1710, 965.

Nuclear magnetic resonance spectrum (CDCl$_3$) δ ppm: 1.60(3H, singlet); 1.70(3H, singlet); 3.92(2H, multiplet); 5.33(2H, multiplet); 5.63(2H, multiplet).

EXAMPLE 13

Methyl ester of 6,9α-methylene-11α,15-di(2-tetrahydropyranyloxy)-17R-methyl-20-isopropylideneprost-5,13(E)-dienoic acid Reaction with a ylide solution and treatment of the reaction mixture were conducted in the same manner as in Example 1, but using 1.20 g. of 3α-(2-tetrahydropyranyloxy)-4β-[3'-(2''-tetrahydropyranyloxy)-5'R, 9'-dimethyl-1',8'-decadienyl]-7-oxobicyclo[3 3.0]octane to give 908 mg. of the desired compound as an oil.

Infrared absorption spectrum (liquid film) $\nu_{max}$ cm$^{-1}$: 1740.

Nuclear magnetic resonance spectrum (CDCl$_3$) δ ppm: 0.91(3H, doublet); 3.68(3H, singlet); 5.30(4H, multiplet).

EXAMPLE 14

Methyl ester of 6,9α-methylene-11α,15α-dihydroxy-17R-methyl-20-isopropylideneprost-5,13(E)-dienoic acid and methyl ester of 6,9α-methylene-11α,15β-dihydroxy-17R-methyl-20-isopropylideneprost-5,13(E)-dienoic acid Reaction with a solution of acetic acid and treatment of the reaction mixture were conducted in the same manner as in Example 3, but using 1.15 g. of the methyl ester of 6,9α-methylene-11α,15-di(2'-tetrahydropyranyloxy)-17R-methyl-20-isopropylideneprost-5,13(E)-dienoic acid, to give the 15β-isomer from the less polar fractions (2 spots-this mixture can be resolved into two optical isomers). Subsequently, optical isomer I of the 15α-isomer was obtained from the fractions more polar than that of the 15β-isomer and optical isomer II of the 15α-isomer was obtained from the most polar fractions.

15β-isomer:

Infrared absorption spectrum (liquid film) $\nu_{max}$ cm$^{-1}$: 1735, 3400

Nuclear magnetic resonance spectrum (CDCl$_3$) δ ppm: 0.90(3H, doublet); 3.63(3H, singlet); 5.10(2H, multiplet); 5.53(2H, multiplet);

optical isomer I of 15α-isomer:

Infrared absorption spectrum (liquid film) $\nu_{max}$ cm$^{-1}$: 1750, 3400.

Nuclear magnetic resonance spectrum (CDCl$_3$) δ ppm: 0.91(3H, doublet); 3.68(3H, singlet); 5.18(2H, multiplet); 5.48(2H, multiplet).

optical isomer II of 15α-isomer:

Infrared absorption spectrum (liquid film) $\nu_{max}$ cm$^{-1}$: 1740, 3400.

Nuclear magnetic resonance spectrum (CDCl$_3$) δ ppm: 0.90(3H, doublet); 3.63(3H, singlet); 5.15(2H, multiplet); 5.48(2H, multiplet).

EXAMPLE 15

6,9α-Methylene-11α,15β-dihydroxy-17R-methyl-20-isopropylideneprost-5,13(E)-dienoic acid

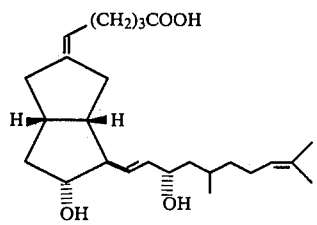

Hydrolysis and treatment of the reaction mixture were conducted in the same manner as in Example 5, but using 290 mg. of the methyl ester of 6,9α-methylene-11α,15β-dihydroxy-17R-methyl-20-isopropylideneprost-5,13(E)-dienoic acid to give the desired compound as an oil.

Infrared absorption spectrum (liquid film) $\nu_{max}$ cm$^{-1}$: 1710, 3350.

Nuclear magnetic resonance spectrum (CDCl$_3$) δ ppm: 0.90(3H, doublet); 1.61(3H, singlet); 1.70(3H, singlet); 5.20(2H, multiplet); 5.60(2H, multiplet).

EXAMPLE 16

6,9α-Methylene-11α,15α-dihydroxy-17R-methyl-20-isopropylideneprost-5(Z),13(E)-dienoic acid (optical isomer I) and 6,9α-methylene-11α,15α-dihydroxy-17R-methyl-20-isopropylideneprost-5(E),13(E)-dienoic acid (optical isomer I)

Hydrolysis and treatment of the reaction mixture were conducted in the same manner as in Example 5, but using 93 mg. of the methyl ester of 6,9α-methylene-11α,15α-dihydroxy-17R-methyl-20-isopropylideneprost-5,13(E)-dienoic acid (optical isomer I) to give the desired compound (5Z-isomer) as an oil from the less polar fractions and another desired compound (5E-isomer) as an oil from the more polar fractions.

5Z-isomer (optical isomer I):

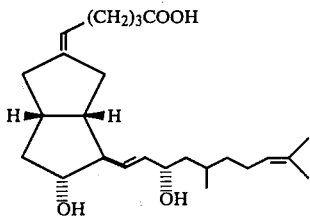

Infrared absorption spectrum (liquid film) $\nu_{max}$ cm$^{-1}$: 1710, 3350.

Nuclear magnetic resonance spectrum (CDCl$_3$) δ ppm: 0.91(3H, doublet); 1.61(3H, singlet); 1.68(3H, singlet); 5.17(2H, multiplet); 5.48(2H, multiplet);

5E-isomer (optical isomer I):

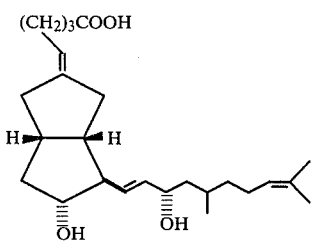

Infrared absorption spectrum (liquid film) $\nu_{max}$ cm$^{-1}$: 1710, 3350.

Nuclear magnetic resonance spectrum (CDCl$_3$) δ ppm: 0.92(3H, doublet); 1.61(3H, singlet); 1.68(3H, singlet); 5.17(2H, multiplet); 5.48(2H, multiplet);

$[\alpha]_D^{20} = +28.1°$ (C=1, CHCl$_3$).

EXAMPLE 17

6,9α-Methylene-11α,15α-dihydroxy-17R-methyl-20-isopropylideneprost-5(Z),13(E)-dienoic acid (optical isomer II) and 6,9α-methylene-11α,15α-dihydroxy-17R-methyl-20-isopropylideneprost-5(E),13(E)-dienoic acid (optical isomer II)

Hydrolysis and treatment of the reaction mixture were conducted in the same manner as in Example 5, but using 91 mg. of the methyl ester of 6,9α-methylene-11α,15α-dihydroxy-17R-methyl-20 -isopropylideneprost-5,13(E)-dienoic acid (optical isomer II) to give a compound (5Z-isomer) as an oil from the less polar fractions and another compound (5E-isomer) as an oil from the more polar fractions.

5Z-isomer (optical isomer II):

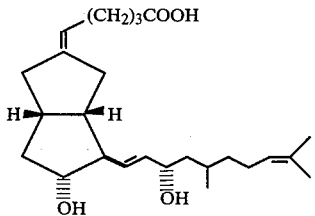

Infrared absorption spectrum (liquid film) $\nu_{max}$ cm$^{-1}$: 1710, 3350.

Nuclear magnetic resonance spectrum (CDCl$_3$) δ ppm: 0.90(3H, doublet); 1.60(3H, singlet); 1.68(3H, singlet); 5.18(2H, multiplet); 5.47(2H, multiplet).

5-isomer (optical isomer II):

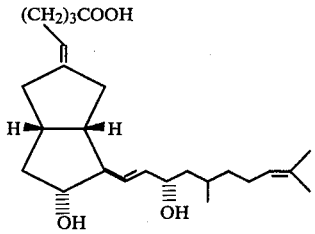

Infrared absorption spectrum (liquid film) $\nu_{max}$ cm$^{-1}$: 1710, 3350.

Nuclear magnetic resonance spectrum (CDCl$_3$) δ ppm: 0.90(3H, doublet); 1.60(3H, singlet); 1.68(3H, singlet); 5.18(2H, multiplet); 5.47(2H, multiplet).

$[\alpha]_D^{20} = -38.2°$ (C=1, CHCl$_3$).

PREPARATION 1

3α-(3-Phenylpropyl)-4α-carboxycyclopentanone

In a mixture of 300 ml. of acetic acid and 300 ml. of dilute aqueous hydrochloric acid were dissolved 83.5 g. of 2β,4α-dimethoxycarbonyl-3α-(3-phenylpropyl-cyclopentanone [which had been prepared according to the method described in Tetrahedron Letters, 101(1976)], and the resulting mixture was refluxed under heating for 2 hours and 45 minutes. Thereafter, a saturated aqueous solution of sodium chloride was added thereto and the resulting mixture was extracted with ethyl acetate. After the extract had been washed with water and dried, the solvent was removed by distillation. The residue thus obtained was purified by silica gel column chromatography to afford 52.1 g. of the desired compound as a crystalline compound. The crystalline compound was recrystallized from a mixed solvent of ethyl acetate and hexane (3:7 by volume) to give crystals melting at 76° to 78° C.

Infrared absorption spectrum (melted film) $\nu$max cm$^{-1}$: 1705, 1740

Nuclear magnetic resonance spectrum (CDCl$_3$) δ ppm: 7.22(5H, singlet); 10.47(1H, singlet).

PREPARATION 2

3α-(3'-Phenylpropyl)-4α-methoxycarbonylmethylcyclopentanone

To 2 ml. of a solution of 496 mg. of 3α-(3'-phenylpropyl)-4α-carboxycyclopentanone dissolved in benzene was added 2 ml. of oxalyl chloride and the resulting mixture was refluxed under heating for 30 minutes. After completion of the reaction, the solvent was removed by distillation. To the residue thus obtained was added a solution of diazomethane in ether (prepared by using 7 g. of Diazald) and the resulting mixture was stirred for 1 hour. Thereafter, the solvent was removed by distillation and the residue thus obtained (containing crude diazoketone compound) was dissolved in a mixture of 10 ml. of methanol and 5 ml. of triethylamine. To the resulting solution was added 1 g. of silver benzoate and the resulting mixture was stirred for 20 minutes. After completion of the reaction, the solvent was evaporated and the residue was extracted with ethyl acetate after addition of a saturated aqueous sodium chloride. After the extract was washed with water and dried, the solvent was removed by distillation. The thus obtained residue was purified by silica gel chromatography to afford 399 mg. of the desired compound as an oil.

Infrared absorption spectrum (liquid film) $\nu$max cm$^{-1}$: 1742

Nuclear magnetic resonance spectrum (CDCl$_3$) δ ppm: 3.72(3H, singlet); 7.34(5H, singlet).

PREPARATION 3

3α-(3'-Phenyl-2'-propenyl)-4α-methoxycarbonylmethylcyclopentanone

To 6 ml. of a solution of 376 mg. of 3α-(3'-phenylpropyl)-4α-methoxycarbonylmethylcyclopentanone in carbon tetrachloride were added 200 mg. of N-bromosuccinimide and a catalytic amount of azobisdiisobutyronitrile, and the resulting mixture was refluxed under heating. After completion of the reaction, the succinimide was removed by filtration and the solvent was removed from the filtrate by distillation to obtain a crude bromo-compound. The crude bromo-compound was dissolved in 10 ml. of tetrahydrofuran and the resulting solution was added dropwise at room temperature to an ethanolic solution of sodium selenophenol [prepared by using 240 mg. of diphenyl diselenide, 64 mg. of sodium borohydride and 10 ml. of ethanol] and the mixture was stirred for 30 minutes. After addition of 2 g. of magnesium sulfate, 0.6 ml. of a 30% aqueous hydrogen peroxide was added dropwise thereto. After stirring for 2 hours, a diluted aqueous sodium bicarbonate was added thereto and the mixture was extracted with ethyl acetate. After the extract was washed with water and dried, the solvent was removed by distillation. The residue thus obtained was purified by silica gel column chromatography to give 322 mg. of the desired compound as an oil.

Infrared absorption spectrum (liquid film) $\nu$max $cm^{-1}$: 1738

Nuclear magnetic resonance spectrum (CDCl$_3$) $\delta$ ppm: 3.70(3H, singlet); 6.12(1H, multiplet); 6.55(1H, doublet); 7.36(5H, singlet).

PREPARATION 4

3α,4α-Dimethoxycarbonylmethylcyclopentanone

To 4 ml. of a solution of 85 mg. of 3α-(3'-phenyl-2'-propenyl)-4α-methoxycarbonylmethylcyclopentanone dissolved in tetrahydrofuran were added 2 ml. of water and 200 mg. of sodium metaperiodate, and then a catalytic amount of osmium tetraoxide, and the resulting mixture was stirred at room temperature for 2 hours and 15 minutes. Thereafter, the solvent was removed by distillation and the residue was extracted with ethyl acetate after addition of a saturated aqueous sodium chloride thereto. After the extract was washed with water and dried, the solvent was removed by distillation. The thus obtained residue was dissolved in 3 ml. of acetone, 0.5 ml. of Jones reagent was added to the resulting solution under ice-cooling and then the mixture was allowed to stand for 15 minutes. After completion of the reaction, the excess amount of the reagent was decomposed with isopropyl alcohol and, after addition of a saturated aqueous sodium chloride, the mixture was extracted with ethyl acetate. After the extract was washed with water and dried, the solvent was removed by distillation. The crude carboxy-compound thus obtained was purified, after esterified with diazomethane dissolved in ether, by silica gel chromatography to give 60 mg. of the desired compound as an oil.

Infrared absorption spectrum (liquid film) $\nu$max $cm^{-1}$: 1735

Nuclear magnetic resonance spectrum (CDCl$_3$) $\delta$ppm: 3.78(6H, singlet).

PREPARATION 5

1,1'-Ethylenedioxy-3α,4α-dimethoxycarbonylmethylcyclopentane

To 50 ml. of a solution of 470 mg. of 3α,4α-dimethoxycarbonylmethylcyclopentanone dissolved in benzene were added 2 ml. of ethylene glycol and a catalytic amount of p-toluenesulfonic acid, and the resulting mixture was heated under dehydration conditions. After completion of the reaction, a diluted aqueous sodium bicarbonate was added thereto and the resulting mixture was extracted with ethyl acetate. After the extract was washed with water and dried, the solvent was removed by distillation. The residue thus obtained was purified by silica gel chromatography to give 336 mg. of the desired compound as an oil.

Infrared absorption spectrum (liquid film) $\nu$max $cm^{-1}$: 1740

Nuclear magnetic resonance spectrum (CDCl$_3$) $\delta$ppm: 3.70(6H, singlet); 3.90(4H, singlet).

PREPARATION 6

4β-Methoxycarbonyl-7,7'-ethylenedioxybicyclo[3.3.0]octan-3-one

To 5 ml. of a solution of 120 mg. of 1,1'-ethylenedioxy-3α,4α-dimethoxycarbonylmethylcyclopentane dissolved in dimethyl sulfoxide was added 0.8 ml. of a methanolic solution of sodium methoxide (containing sodium methoxide corresponding to 9.5 mg. of Na), and the resulting mixture was heated for 30 minutes at a temperature at which methanol was distilled out. Thereafter, the mixture was allowed to stand at room temperature for 1 hour, neutralized with aqueous acetic acid and then extracted with ethyl acetate. After the extract was washed with water and dried, the solvent was removed by distillation. The residue thus obtained was purified by silica gel column chromatography to give 73 mg. of the desired compound as an oil.

Infrared absorption spectrum (liquid film) $\nu$max $cm^{-1}$: 1620, 1665, 1730, 1755

Nuclear magnetic resonance spectrum (CDCl$_3$) $\delta$ppm: 3.78(3H, singlet); 3.90(4H, singlet).

PREPARATION 7

3α-Hydroxy-4β-methoxycarbonyl-7,7'-ethylenedioxybicyclo[3.3.0]octane

To 5 ml. of a solution of 250 mg. of 4β-methoxycarbonyl-7,7'-ethylenedioxybicyclo[3.3.0]octan-3-one dissolved in anhydrous methanol was added 35 mg. of sodium borohydride under ice-cooling. After 13 minutes, the excess reagent was decomposed with acetic acid; a saturated aqueous sodium chloride was added thereto; and the resulting mixture was extracted with ethyl acetate. After the extract was washed with water and dried, the solvent was removed by distillation. The residue thus obtained was purified by silica gel column chromatography to give 145 mg. of the desired compound as an oil.

Infrared absorption spectrum (liquid film) $\nu$max $cm^{-1}$: 1730, 3450

Nuclear magnetic resonance spectrum (CDCl$_3$) $\delta$ppm: 3.75(3H, singlet); 3.98(4H, singlet); 4.33(1H, multiplet).

PREPARATION 8

3α-(2'-Tetrahydropyranyloxy)-4β-methoxycarbonyl-7,7'-ethylenedioxybicyclo[3.3.0]octane To 5 ml. of a solution of 140 mg. of 3α-hydroxy-4β-methoxycarbonyl-7,7'-ethylenedioxybicyclo[3.3.0]octane in anhydrous benzene were added 0.6 ml. of dihydropyran and a catalytic amount of picric acid, and the resulting mixture was allowed to stand for 1 hour under ice-cooling. Thereafter, ethyl acetate was added to the reaction mixture, and the resulting mixture was dried after washing in turn with diluted aqueous sodium bicarbonate and water. The residue which was obtained after removal of the solvent by distillation was purified by column chromatography using alumina (Grade III) to give 173 mg. of the desired compound as an oil.

Infrared absorption spectrum (liquid film) νmax cm⁻¹: 1735

Nuclear magnetic resonance spectrum (CDCl₃) δppm: 3.70(3H, singlet); 3.90(4H, singlet); 4.62(1H, multiplet).

PREPARATION 9

3α-(2'-Tetrahydropyranyloxy)-4β-hydroxymethyl-7,7'-ethylenedioxybicyclo[3.3.0]octane To 7 ml. of a solution of 165 mg. of 3α-(2'-tetrahydropyranyloxy)-4β-methoxycarbonyl-7,7'-ethylenedioxybicyclo[3.3.0]octane in ether was added 130 mg. of lithium aluminum hydride under ice-cooling, and the resulting mixture was stirred for 20 minutes. After completion of the reaction, 0.51 ml. of 4% aqueous caustic soda was added thereto and the resulting mixture was stirred at room temperature. The white precipitate thus formed was removed by filtration and the filtrate was concentrated. The thus obtained residue was purified by silica gel column chromatography to give 84 mg. of the desired product as an oil.

Infrared absorption spectrum (liquid film) νmax cm⁻¹: 3450

Nuclear magnetic resonance spectrum (CDCl₃) δppm: 3.82(4H, singlet); 4.55(1H, multiplet).

PREPARATION 10

3α-(2'-Tetrahydropyranyloxy)-4β-(3'-oxo-1'-octenyl)-7,7'-ethylenedioxybicyclo[3.3.0]octane To 5 ml. of a solution of 100 mg. of 3α-(2'-tetrahydropyranyloxy)-4β-hydroxymethyl-7,7'-ethylenedioxybicyclo[3.3.0]octane in 5 ml. of methylene chloride were added a solution of chromic anhydride-pyridine complex in methylene chloride (prepared with 500 mg. of chromic anhydride, 0.7 ml. of pyridine and 15 ml. of methylene chloride), and the resulting mixture was allowed to stand for 10 minutes under ice-cooling. After completion of the reaction, an excess amount of ether was added thereto and the organic layer was washed in turn with a saturated aqueous sodium chloride, a diluted aqueous sodium bicarbonate and then a saturated aqueous sodium chloride. After drying, the solvent was removed by distillation. The crude aldehyde compound thus obtained was dissolved without purification in 5 ml. of ether and, after addition of 130 mg. of 2-oxoheptylidenetrinormalbutylphosphorane, the resulting mixture was allowed to stand at room temperature overnight. Thereafter, the solvent was removed by distillation and the resulting residue was purified by silica-gel column chromatography to give 98 mg. of the desired compound as an oil.

Infrared absorption spectrum (liquid film) νmax cm⁻¹: 1620, 1670, 1685

Nuclear magnetic resonance spectrum (CDCl₃) δppm: 3.90(4H, singlet); 4.65(1H, multiplet); 6.50(2H, multiplet).

PREPARATION 11

3α-(2'-Tetrahydropyranyloxy)-4β-(3'-hydroxy-1'-octenyl)-7,7'-ethylenedioxybicyclo[3.3.0]octane To 6 ml. of a solution of 95 mg. of 3α-(2'-tetrahydropyranyloxy)-4β-(3'-oxo-1'-octenyl)-7,7'-ethylenedioxybicyclo[3.3.0]octane in anhydrous methanol was added 150 mg. of sodium borohydride under ice-cooling, and the resulting mixture was allowed to stand for 10 minutes. Then, acetic acid was added thereto to decompose the excess reagent and a saturated aqueous sodium chloride was added thereto, followed by extraction with ethyl acetate. After the extract was washed with water and dried, the solvent was removed by distillation to give the desired compound as an oil.

Infrared absorption spectrum (liquid film) νmax cm⁻¹: 3450

Nuclear magnetic resonance spectrum (CDCl₃) δppm: 0.90(3H, triplet); 3.90(4H, singlet); 4.67(1H, muliplet); 5.58(2H, multiplet).

PREPARATION 12

3α-Hydroxy-4β-(3'α-hydroxy-1'-octenyl)-7-oxobicyclo[3.3.0]octane and
3α-hydroxy-4β-(3'β-hydroxy-1'-octenyl)-7-oxobicyclo[3.3.0]octane To 100 ml. of a solution of 4.80 g. of 3α-(2'-tetrahydropyranyloxy)-4β-(3'-hydroxy-1'-octenyl)-7,7'-ethylenedioxybicyclo[3.3.0]octane in an aqueous acetone (water:acetone=3:7) was added 2.5 ml. of conc. hydrochloric acid, and the resulting mixture was allowed to stand for 1 hour under ice-cooling and further for 2 hours at room temperature. Then, a diluted aqueous sodium bicarbonate and a saturated aqueous sodium chloride were added thereto, followed by extraction with ether. After the extract was washed with water and dried, the solvent was removed by distillation. The residue thus obtained was purified by silica gel column chromatography to give 580 mg. of a desired compound (3'β-isomer) as an oil from the less polar fractions and 1.267 g. of another desired compound (3'α-isomer) as an oil from the more polar fractions.

3'β-isomer:
Infrared absorption spectrum (liquid film) νmax cm⁻¹: 1732, 3380

Nuclear magnetic resonance spectrum (CDCl₃) δppm: 0.90(3H, triplet); 4.03(2H, multiplet); 5.61(2H, multiplet).

3'α-isomer:
Infrared absorption spectrum (liquid film) νmax cm⁻¹: 1733, 3380

Nuclear magnetic resonance spectrum (CDCl₃) δppm: 0.89(3H, triplet); 3.80(2H, multiplet); 5.50(2H, multiplet).

PREPARATION 13

3α-(2'-Tetrahydropyranyloxy)-4β-[3'α-(2''-tetrahydropyranyloxy)-1'-octenyl]-7-oxobicyclo[3.3.0]octane To 12 ml. of a solution of 500 mg. of 3α-hydroxy-4β-(3'α-hydroxy-1'-octenyl)-7-oxobicyclo[3.3.0]octane in anhydrous benzene were added 8 ml. of dihydropyran and a catalytic amount of picric acid, and the resulting mixture was allowed to stand at room temperature for 2 hours. Thereafter, the reaction mixture was purified as such by column chromatography using alumina to give 800 mg. of the desired compound as an oil.

Infrared absorption spectrum (liquid film) νmax cm⁻¹: 1740

Nuclear magnetic resonance spectrum (CDCl₃) δppm: 0.90(3H, triplet); 4.67(2H, multiplet); 5.50(2H, multiplet).

PREPARATION 14

3α-(2'-Tetrahydropyranyloxy)-4β-[3'β-(2''-tetrahydropyranyloxy)-1'-octenyl]-7-oxobicyclo[3.3.0]octane Reaction with dihydropyran and after-treatment of the reaction mixture were conducted in the same manner as in Preparation 13, but using 710 mg. of 3α-hydroxy-4β-(3'β-hydroxy-1'-octenyl)-7-oxobicyclo[3.3.0]octane to obtain 1.247 g. of the desired compound as an oil.

Infrared absorption spectrum (liquid film) $\nu$max cm$^{-1}$: 1740

Nuclear magnetic resonance spectrum (CDCl$_3$) $\delta$ppm: 0.89(3H, triplet); 4.66(2H, multiplet); 5.50(2H, multiplet).

PREPARATION 15

3α-(2'-Tetrahydropyranyloxy)-4β-(3'-oxo-9'-methyl-1',8'-decadienyl)-7,7'-ethylenedioxybicyclo[3.3.0]octane After 648 mg. of a 52.9% sodium hydride in oil was washed with anhydrous petroleum ether to remove the oil, the resultant was suspended in 25 ml. of tetrahydrofuran. To the suspension was added dropwise 15 ml. of a solution of 5.08 g. of 2-oxo-8-methyl-7-nonenylphosphonate in tetrahydrofuran and the resulting mixture was stirred further for 3 hours and 30 minutes. To the solution was added 20 ml. of a solution in tetrahydrofuran of 2.50 g. of 3α-(2'-tetrahydropyranyloxy)-4β-formyl-7,7'-ethylenedioxybicyclo[3.3.0]octane which had been prepared in the same manner as in Preparation 10 and the resulting mixture was stirred further for 45 minutes. After completion of the reaction, acetic acid and then a saturated aqueous sodium chloride were added to the reaction mixture, followed by extraction with ether. After the extract was washed with water and dried, the solvent was removed by distillation. The residue thus obtained was purified by column chromatography using alumina to give the desired compound as an oil.

Infrared absorption spectrum (liquid film) $\nu$max cm$^{-1}$: 1630, 1675, 1700

Nuclear magnetic resonance spectrum (CDCl$_3$) $\delta$ppm: 1.60(3H, singlet); 1.78(3H, singlet); 3.93(4H, singlet); 4.70(1H, multiplet); 5.18(1H, triplet); 6.50(2H, multiplet).

PREPARATION 16

3α-(2'-Tetrahydropyranyloxy)-4β-(3'-hydroxy-9'-methyl-1',8'-decadienyl)-7,7'-ethylenedioxybicyclo[3.3.0]octane Reduction reaction and after-treatment of the reaction mixture were conducted in the same manner as in Preparation 11, but using 290 mg. of 3α-(2'-tetrahydropyranyloxy)-4β-(3'-oxo-9'-methyl-1',8'-decadienyl)-7,7'-ethylenedioxybicyclo[3.3.0]octane to obtain the desired compound as an oil.

Infrared absorption spectrum (liquid film) $\nu$max cm$^{-1}$: 3450

Nuclear magnetic resonance spectrum (CDCl$_3$) $\delta$ppm: 3.87(4H, singlet); 4.62(1H, multiplet); 5.10(1H, triplet); 5.54(2H, multiplet).

PREPARATION 17

3α-Hydroxy-4β-(3'β-hydroxy-9'-methyl-1',8'-decadienyl)-7-oxobicyclo[3.3.0]octane and
3α-hydroxy-4β-(3'α-hydroxy-9'-methyl-1',8'-decadienyl)-7-oxobicyclo[3.3.0]octane Reaction with a solution of hydrochloric acid and aftertreatment of the reaction mixture were conducted in the same manner as in Preparation 12, but using 3.485 g. of 3α-(2'-tetrahydropyranyloxy)-4β-(3'-hydroxy-9'-methyl-1',8'-decadienyl)-7,7'-ethylenedioxybicyclo[3.3.0]octane to obtain a desired compound (3'β-isomer) as an oil from the less polar fractions and another desired compound (3'α-isomer) as an oil from the more polar fractions.

3'β-isomer:

Infrared absorption spectrum (liquid film) $\nu$max cm$^{-1}$: 3400, 1735

Nuclear magnetic resonance spectrum (CDCl$_3$) $\delta$ppm: 1.80(3H, singlet); 1.70(3H, singlet); 5.15(1H, triplet); 5.61(2H, multiplet).

3'α-isomer:

Infrared absorption spectrum (liquid film) $\nu$max cm$^{-1}$: 3400, 1735

Nuclear magnetic resonance spectrum (CDCl$_3$) $\delta$ppm: 1.57(3H, singlet); 1.65(3H, singlet); 5.10(1H, triplet); 5.50(2H, multiplet).

PREPARATION 18

3α-(2'-Tetrahydropyranyloxy)-4β-[3'α-(2''-tetrahydropyranyloxy)-9'-methyl-1',8'-decadienyl]-7-oxobicyclo[3.3.0]octane Reaction with dihydropyran and after-treatment of the reaction mixture were conducted in the same manner as in Preparation 13, but using 910 mg. of 3α-hydroxy-4β-(3'α-hydroxy-9'-methyl-1',8'-decadienyl)-7-oxobicyclo[3.3.0]octane to give the desired compound as an oil.

Infrared absorption spectrum (liquid film) $\nu$max cm$^{-1}$: 1740

Nuclear magnetic resonance spectrum (CDCl$_3$) $\delta$ppm: 5.10(1H, triplet); 5.50(2H, multiplet).

PREPARATION 19

3α-(2'-Tetrahydropyranyloxy)-4β-[3'β-(2''-tetrahydropyranyloxy)-9'-methyl-1',8'-decadienyl]-7-oxobicyclo[3.3.0]octane Reaction with dihydropyran and after-treatment of the reaction mixture were conducted in the same manner as in Preparation 13, but using 510 mg. of 3α-hydroxy-4β-(3'β-hydroxy-9'-methyl-1',8'-decadienyl)-7-oxobicyclo[3.3.0]octane to obtain the desired compound as an oil.

Infrared absorption spectrum (liquid film) $\nu$max cm$^{-1}$: 1740

Nuclear magnetic resonance spectrum (CDCl$_3$) $\delta$ppm: 5.10(1H, triplet); 5.60(2H, multiplet).

PREPARATION 20

3α-(2'-Tetrahydropyranyloxy)-4β-(3'-oxo-5'R,9'-dimethyl-1',8'-decadienyl)-7,7'-ethylenedioxy-cis bicyclo[3.3.0]octane Reaction and after-treatment were conducted in the same manner as in Preparation 15, but using 327 mg. of a 52.9% sodium hydride in oil, 2.74 g. of dimethyl 2-oxo-4R,8-dimethyl-7-nonenylphosphonate and 1.20 g. of 3α-(2'-tetrahydropyranyloxy)-4β-formyl-7,7'-ethylenedioxybicyclo[3.3.0]octane which had been prepared according to the same procedure as in Preparation 10 to give the desired product as an oil.

Infrared absorption spectrum (liquid film) $\nu$max cm$^{-1}$: 1625, 1665, 1690

Nuclear magnetic resonance spectrum (CDCl$_3$) $\delta$ppm: 0.90(3H, doublet); 1.62(3H, singlet); 1.67(3H, singlet); 3.94(4H, singlet); 6.50(2H, multiplet).

PREPARATION 21

3α-(2'-Tetrahydropyranyloxy)-4β-(3'-dihydroxy-5'R,9'-dimethyl-1',8'-decadienyl)-7,7'-ethylenedioxybicyclo[3.3.0]octane Reduction reaction and after-treatment of the reaction mixture were conducted in the same manner as in Preparation 11, but using 1.35 g. of 3α-(2'-tetrahydropyranyloxy)4β-(3'-oxo-5'R,9'-dimethyl-1',8'-decadienyl)-7,7'-ethylenedioxy-cis-bicyclo[3.3.0]octane to obtain the desired compound as an oil.

Infrared absorption spectrum (liquid film) νmax cm$^{-1}$: 3480

Nuclear magnetic resonance spectrum (CDCl$_3$) δppm: 3.88(4H, singlet); 5.08(1H, multiplet); 5.52(2H, multiplet).

PREPRATION 22

3α-Hydroxy-4β-(3'-hydroxy-5'R,9'-dimethyl-1',8'-decadienyl)-7-oxobicyclo[3.3.0]octane Reaction with a solution of hydrochloric acid and after-treatment of the reaction mixture were conducted in the same manner as in Preparation 12, but using 1.31 g. of 3α-(2'-tetrahydropyranyloxy)-4β-(3'-hydroxy-5'R,9'-dimethyl-1'8'-decadienyl)-7,7'-ethylenedioxybicyclo[3.3.0]octane to obtain the desired compound (a mixture of the isomers with respect to the 3'-position) as an oil.

This reaction proceeds similarly when acetic acid and water were used.

Infrared absorption spectrum (liquid film) νmax cm$^{-1}$: 1740, 3400

Nuclear magnetic resonance spectrum (CDCl$_3$) δppm: 0.91(3H, doublet);
1.60(3H, singlet); 1.67(3H, singlet); 5.02(1H, multiplet); 5.50(2H, multiplet).

PREPARTION 23

3α-(2'-Tetrahydropyranyloxy)-4β-[3'-(2''-tetrahydropyranyloxy)-5'R,9'-dimethyl-1',8'-decadienyl]-7-oxobicyclo [3.3.0]octane Reaction and after-treatment of the reaction mixture were conducted in the same manner as in Preparation 13 by using 830 mg. of 3α-hydroxy-4β-(3'-hydroxy-5'R,9'-dimethyl-1',8'-decadienyl)-7-oxobicyclo[3.3.0]octane to give the desired compound as an oil.

Infrared absorption spectrum (liquid film) νmax cm$^{-1}$: 1740

Nuclear magnetic resonance spectrum (CDCl$_3$) δppm: 0.92(3H, doublet); 4.66(2H, multiplet).

PREPARATION 24

4α,5α-Dihydroxymethyl-1-cyclohexene

In 100 ml. of dehydrated tetrahydrofuran was suspended 5 g. of lithium aluminum hydride, and 7 g. of 4α,5α-dicarboxy-1-cyclohexene was added gradually thereto. After completion of the addition, the mixture was heated under reflux for 4 hours. After completion of the reaction, the reagent was decomposed with a saturated aqueous sodium sulfate (33 ml.), and the white precipitates were removed by filtration. The filtrate was concentrated to give 6.0 g. of the desired product as an oily substance.

Infrared (IR) spectrum (liquid film) $\nu_{max}$ cm$^{-1}$: 3320

Nuclear Mag Resonance (NMR) spectrum (CDCl$_3$) δppm: 5.61 (2H multiplet).

PREPARATION 25

4α,5α-Dimethanesulfonyloxymethyl-1-cyclohexene

To 2.11 ml. of a solution of 31.2 g. of methanesulfonyl chloride in pyridine was added gradually dropwise at −10° C. to 0° C. 5 ml. of a solution of 1.30 g. of 4α,5α-dihydroxymethyl-1-cyclohexene in pyridine. Thereafter, the reaction mixture was allowed to stand at the same temperature for 2 hours and 56 ml. of a diluted aqueous hydrochloric acid was added thereto, with keeping the reaction mixture at not more than 5° C.

The precipitated crystals were collected by filtration to give 2.33 g. of the desired product. The product was recrystallized from a mixed solvent of ethyl acetate-hexane (1:1 v/v) to give crystals melting at 84° C. to 85° C.

IR spectrum (Nujol) $\nu_{max}$ cm$^{-1}$: 1340

NMR spectrum (CDCl$_3$) δppm: 3.03 (6H singlet), 4.12 (4H multiplet), 5.70 (2H multiplet).

PREPARATION 26

4α,5α-Dicyanomethyl-1-cyclohexene

To 200 g. of a solution of 8.5 g. of sodium cyanide in dimethyl sulfoxide was added 23.3 g. of 4α,5α-dimethanesulfonylhydroxymethyl-1-cyclohexene, and the mixture was heated at 100° C. to 105° C. for 3 hours with stirring. After cooling, an ice-water was added thereto, and the reaction mixture was extracted with ethyl acetate. After the extract was washed with water and dried, the solvent was removed by distillation. The thus obtained residue was crystallized from mixed solvent of ethyl acetatehexane to give 9.6 g. of the desired product. The product was recrystallized from ethyl acetate-hexane (1:1 v/v) to give crystals melting at 43° C. to 45° C.

IR spectrum (Nujol) $\nu_{max}$ cm$^{-1}$: 2260

NMR spectrum (CDCl$_3$) δppm: 5.68 (2H multiplet)

PREPARATION 27

4α,5α-Diethoxycarbonylmethyl-1-cyclohexene

A mixture of 407 mg. of 4α,5α-dicyanomethyl-1-cyclohexene and 5 ml. of ethanol saturated with hydrogen chloride gas was allowed to stand under ice-cooling for 4 hours and 30 minutes. Thereafter, the solvent was removed by distillation, and water was added to the residue thus obtained, and then the mixture was stirred at room temperature of 1.5 hours. The aqueous solution was extracted with ethyl acetate. The extract was washed with water and dried over anhydrous sodium sulfate, followed by removal of the solvent by filtration. The residue thus obtained was purified by column chromatography using 15 g. of silica gel to give 308 mg. of the desired product as an oily substance from the fraction eluted with a 1% to 3% ethyl acetate-toluene, IR spectrum (liquid film) $\nu_{max}$cm$^{-1}$: 1735

NMR spectrum (CDCl$_3$) δppm: 1.22 (6H multiplet), 4.10 (4H quartet), 5.59 (2H multiplet).

PREPARATION 28

7β-Ethoxycarbonyl-8-oxo-cis-bicyclo[4.3.0]nonene-3

To 150 ml. of a solution of 14.3 g. of 4α,5α-diethoxycarbonylmethyl-1-cyclohexene in dimethyl sulfoxide was added a solution of sodium ethoxide in ethanol prepared from 2.2 g. of metallic sodium and 50 ml. of ethanol, and the mixture was heated. After completion of the reaction, the reaction mixture was cooled, and an ice was added thereto, and then the resulting crystals precipitated were collected by filtration (8.2 g.). The crystals were recrystallized from 50% v/v aqueous ethanol to yield crystals melting at 40° C. to 41° C.

IR spectrum (Nujol) $\nu_{max}$ cm$^{-1}$: 1720, 1743

NMR spectrum (CDCl$_3$) δppm: 1.25 (3H triplet), 4.18 (2H quartet), 5.68 (2H multiplet).

PREPARATION 29

8-Oxo-cis-bicyclo[4.3.0]nonene-3

To 40 ml. of a solution of 8.0 g. of 7β-ethoxycarbonyl-8-oxo-cis-bicyclo[4.3.0]nonene-3 in acetic acid was added 40 ml. of a diluted aqueous hydrochloric acid, and the mixture was heated under reflux for 4 hours. After addition of a saturated aqueous sodium chloride thereto, the mixture was extracted with ethanol. The extract was washed with a saturated aqueous sodium bicarbonate followed by water, and then dried over anhydrous sodium sulfate. The solvent was removed by distillation to afford 4.00 g. of the desired product as an oily substance.

IR spectrum (liquid film) $\nu_{max}$ cm$^{-1}$: 1740

NMR spectrum (CDCl$_3$) δppm: 5.64 (2H multiplet)

PREPARATION 30

3α,4α-Dimethoxycarbonylmethyl-cyclopentanone

To 20 ml. of a solution of 1 g. of 8-oxo-cis-bicyclo[4.3.0]nonene-3 in tetrahydrofuran were added 8 ml. of water and 4.3 g. of sodium metaperiodate. Then, a catalytic amount of osmium tetraoxide was added thereto, and the mixture was stirred at room temperature for 1 hour and 15 minutes. A large amount of ether was added thereto, and the other layer was dried over anhydrous sodium sulfate. The solvent was removed by distillation, and the residue thus obtained (dialdehyde compound: IR spectrum (liquid film) $\nu_{max}$ cm$^{-1}$: 2720, 1710) was dissolved in 5 ml. of acetone. An excess amount of Jones reagent was added thereto, and the mixture was allowed to stand for 40 minutes. After completion of the reaction, the excess amount of the reagent was decomposed with isopropyl alcohol, ether was added thereto, and the ether layer was dried over anhydrous sodium sulfate. The solvent was removed by distillation and the residue thus obtained was treated by diazomethane, followed by purification by column chromatography using 20 g. of silica gel to obtain 679 mg. of an oily desired product from the fraction eluted with a 15% to 30% ethyl acetate-hexane.

IR spectrum (liquid film ) $\nu_{max}$ cm$^{-1}$: 1735

NMR spectrum (CDCl$_3$) δppm: 3.78 (6H singlet)

PREPARATION 31

8,8'-Ethylenedioxy-cis-bicyclo[4.3.0]nonene-3

Acetalization and treatment of the reaction mixture was conducted in the same manner as in Preparation 5, but using 1.0 g of 8-oxo-cis-bicyclo[4.3.0]nonene-3 to yield 870 mg of the desired product.

NMR spectrum (CDCl$_3$ δppm: 5.63 (2H multiplet).

PREPARATION 32

1,1'-Ethylenedioxy-3α,4α-dimethoxycarbonylmethyl-cyclopentane

Oxidation and treatment of the reaction mixture were conducted in the same manner as in Preparation 30, but using 465 mg of 8,8'-ethylenedioxy-cis-bicyclo[4.3.0]nonene-3 to afford the desired product as an oily substance.

IR spectrum (liquid film) $\nu_{max}$ cm$^{-1}$: 1740

NMR spectrum (CDCl$_3$) δppm: 3.70 (6H, singlet); 3.90 (4H, singlet).

We claim:

1. Compounds of formula (I):

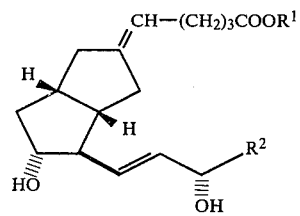

wherein:
R$^1$ represents a hydrogen atom or an alkyl group having from 1 to 15 carbon atoms;
R$^2$ represents a 6-methyl-5-heptenyl group of a 2,6-dimethyl-5-heptenyl group;
and pharmaceutically acceptable salts thereof.

2. Compounds as claimed in claim 1 wherein R$^1$ is a hydrogen atom or an alkyl group having from 1 to 3 carbon atoms; and R$^2$ is a 6-methyl-5-heptenyl group.

3. Compounds as claimed in claim 1 wherein R$^1$ is a hydrogen atom or an alkyl group having from 1 to 3 carbon atoms; and R$^2$ is a 2,6-dimethyl-5-heptenyl group.

4. 6,9α-Methylene-11α,15α-dihydroxy-20-isopropylideneprost-5(Z),13(E)-dienoic acid of the formula of claim 1.

5. 6,9α-Methylene-11α,15β-dihydroxy-20-isopropylideneprost-5(Z),13(E)-dienoic acid of the formula of claim 1.

6. 6,9α-Methylene-11α,15α-dihydroxy-20-isopropylideneprost-5(E),13(E)-dienoic acid, its sodium salt and its methyl ester of the formula of claim 1.

7. 6,9α-Methylene-11α,15β-dihydroxy-20-isopropylideneprost-5(E),13(E)-dienoic acid of the formula of claim 1.

8. 6,9α-Methylene-11α,15α-dihydroxy-17-methyl-20-isopropylideneprost-5(Z),13(E)-dienoic acid of the formula of claim 1.

9. 6,9α-Methylene-11α,15β-dihydroxy-17-methyl-20-isopropylideneprost-5(Z),13(E)-dienoic acid of the formula of claim 1.

10. 6,9α-Methylene-11α,15α-dihydroxy-17-methyl-20-isopropylidenenprost-5(E),13(E)-dienoic acid, its sodium salt and its methyl ester of the formula of claim 1.

11. 6,9α-Methylene-11α,15β-dihydroxy-17-methyl-20-isopropylideneprost-5(E),13(E)-dienoic acid of the formula of claim 1.

12. A composition for the treatment and prophylaxis of thrombosis comprising (i) a pharmaceutically acceptable carrier and (ii) an effective amount of a compound of claim 1.

13. A composition for the treatment and prophylaxis of thrombosis comprising (i) a pharmaceutically acceptable carrier and (ii) an effective amount of a compound of claim 2.

14. A composition for the treatment and prophylaxis of thrombosis comprising (i) a pharmaceutically acceptable carrier and (ii) an effective amount of a compound of claim 3.

15. A composition for the treatment and prophylaxis of thrombosis comprising (i) a pharmaceutically acceptble carrier and (ii) an effective amount of the compound of claim 4.

16. A composition for the treatment and prophylaxis of thrombosis comprising (i) a pharmaceutically acceptable carrier and (ii) an effective amount of the compound of claim 5.

17. A composition for the treatment and prophylaxis of thrombosis comprising (i) a pharmaceutically acceptable carrier and (ii) an effective amount of a compound of claim 6.

18. A composition for the treatment and prophylaxis of thrombosis comprising (i) a pharmaceutically acceptable carrier and (ii) an effective amount of the compound of claim 7.

19. A composition for the treatment and prophylaxis of thrombosis comprising (i) a pharmaceutically acceptable carrier and (ii) an effective amount of the compound of claim 8.

20. A composition for the treatment and prophylaxis of thrombosis comprising (i) a pharmaceutically acceptable carrier and (ii) an effective amount of the compound of claim 9.

21. A composition for the treatment and prophylaxis of thrombosis comprising (i) a pharmaceutically acceptable carrier and (ii) an effective amount of a compound of claim 10.

22. A composition for the treatment and prophylaxis of thrombosis comprising (i) a pharmaceutically acceptable carrier and (ii) an effective amount of the compound of claim 11.

* * * * *

UNITED STATES PATENT AND TRADEMARK OFFICE
CERTIFICATE OF CORRECTION

PATENT NO. : 4,322,435
DATED : March 30, 1982
INVENTOR(S) : KOICHI KOJIMA et al

It is certified that error appears in the above—identified patent and that said Letters Patent is hereby corrected as shown below:

Column 22, line 18: replace "yield" with --ylide--.

Column 26, line 46: replace "5,15(E)" with --5,13(E)--.

Column 29, line 52: replace "5-isomer" with --5E-isomer--.

Column 40, line 22 (Claim 1): after "group" replace "of" with --or--.

Signed and Sealed this

Twenty-seventh Day of July 1982

[SEAL]

Attest:

Attesting Officer

GERALD J. MOSSINGHOFF

Commissioner of Patents and Trademarks